(12) United States Patent
Bassett et al.

(10) Patent No.: US 9,732,321 B2
(45) Date of Patent: Aug. 15, 2017

(54) ENGINEERED CRANIOFACIAL CONSTRUCTS WITH COMPOSITE SCAFFOLD

(75) Inventors: Erik Bassett, Watertown, MA (US);
Mack Cheney, Brookline, MA (US);
Theresa Hadlock, Concord, MA (US);
Irina Pomerantseva, Wakefield, MA (US); Mark Randolph, Chelmsford, MA (US); Cathryn Sundback, Harvard, MA (US); Joseph Vacanti, Winchester, MA (US)

(73) Assignees: THE GENERAL HOSPITAL CORPORATION, Boston, MA (US); MASSACHUSETTS EYE AND EAR INFIMARY, Boston, MA (US)

(*) Notice: Subject to any disclaimer, the term of this patent is extended or adjusted under 35 U.S.C. 154(b) by 111 days.

(21) Appl. No.: 13/028,725

(22) Filed: Feb. 16, 2011

(65) Prior Publication Data
US 2011/0264236 A1    Oct. 27, 2011

Related U.S. Application Data

(60) Provisional application No. 61/304,926, filed on Feb. 16, 2010.

(51) Int. Cl.
| | |
|---|---|
| *A61F 2/02* | (2006.01) |
| *C12N 5/077* | (2010.01) |
| *A61L 27/04* | (2006.01) |
| *A61L 27/24* | (2006.01) |
| *A61L 27/50* | (2006.01) |
| *C12N 5/0775* | (2010.01) |

(52) U.S. Cl.
CPC .......... *C12N 5/0655* (2013.01); *A61L 27/04* (2013.01); *A61L 27/24* (2013.01); *A61L 27/50* (2013.01); *C12N 5/0663* (2013.01); *C12N 2501/15* (2013.01); *C12N 2502/1317* (2013.01); *C12N 2533/54* (2013.01)

(58) Field of Classification Search
CPC ................................. B29C 39/10; A61F 2/02
USPC ....... 623/14.12, 10, 23.72–23.76; 264/271.1, 264/279.1; 435/183, 325, 366
See application file for complete search history.

(56) References Cited

U.S. PATENT DOCUMENTS 5,800,454 A * 9/1998 Jacobsen et al. ............. 606/191
6,509,031 B1   1/2003 Miller et al.
(Continued)

OTHER PUBLICATIONS

Cao et al., "Transplantation of Chondrocytes utilizing a polymer-cell construtct to produce tissue-engineered cartilage in the shape of a human ear", Plast. Reconstr. Surg. 100:297-302 (1997).
(Continued)

*Primary Examiner* — Yashita Sharma
(74) *Attorney, Agent, or Firm* — Nixon Peabody LLP

(57) ABSTRACT

The present invention provides for compositions and constructs for craniofacial reconstruction implants, and methods for making and using same. Specific embodiments provide for a biocompatible scaffold having an auricular shape and a permanent bendable framework within the scaffold, wherein the permanent bendable framework allows deformation and return to pre-deformation shape, and thus maintains the auricular shape of the scaffold.

16 Claims, 15 Drawing Sheets
(9 of 15 Drawing Sheet(s) Filed in Color)

(56) References Cited

U.S. PATENT DOCUMENTS

| | | | |
|---|---|---|---|
| 6,617,431 B1 | 9/2003 | Gruber et al. | |
| 6,653,450 B1 | 11/2003 | Berg et al. | |
| 6,713,662 B1 | 3/2004 | Karatzas et al. | |
| 6,992,172 B1 | 1/2006 | Chang et al. | |
| 7,410,502 B2 | 8/2008 | Ellingsen et al. | |
| 2005/0214340 A1* | 9/2005 | Erbe et al. | 424/423 |
| 2006/0276875 A1* | 12/2006 | Stinson et al. | 623/1.15 |
| 2007/0004035 A1* | 1/2007 | Sitzmann | 435/325 |
| 2009/0228105 A1* | 9/2009 | Son et al. | 623/14.12 |

OTHER PUBLICATIONS

Chetty et al., Hydroxyapatite-coated polyurethane for auricular cartilage replacement: An in vitro study, J. Biomed. Mats. Res. 841:475-482 (2008).

Chung et al., "Influence of gel properties on neocartilage formation by auricular chondrocytes photoencapsulated in hyaluronic acid networks", J. Biomed. Mat. Res. A. 77(3):518-525 (2006).

Chung C. & Burdick J.A., "Influence of 3D hyaluronic acid microenviroments on mesenchymal stem cell chondrogenesis", Adv. Drug Deliv. Rev. 15(2):243-254 (2009).

Fujihara et al., "Immunological response to issue-engineered cartilage derived from auricular chondrocytes and a PLLA scaffold in transgenic mice", Biomats. 31:1227-1234 (2010).

Haisch et al., "A tissue engineering model for the manufacture of auricular shaped cartilage implants", Otorhinolaryngol. 259:316-321 (2002).

Haisch A., "Ear reconstruction through tissue engineering", Adv. Otorhinolaryngol. 68:108-119 (2010).

Heymer et al., "Multiphasic collagen fibre-PLA composites seeded with human mesenchymal stem cells for osteochondral defect repair: an in vivo study", J. Tissue Engin. Regen. Med. 3:389-397 (2009).

Hsu et al., "Evaluation of biodegradable polyesters modified by type II collagen and arg-gly-asp as tissue engineering scaffolding materials for cartilage regeneration", Artif. Organs 30(1):42-55 (2006).

Hwang et al., "Response of zonal chondrocytes to extracellular matrix-hydrogels", FEBS Letters 581:4172-4178 (2007).

Isogai et al., "Combined chondrocyte-copolymer implantation with slow release of basic fibroblast growth factor for tissue engineering an auricular cartilage construct", J. Biomed. Mat. Res. A 74:408-418 (2005).

Isogai et al., "Tissue engineering of an auricular cartilage model utilizing cultured chondrocyte-poly(L-lactide—caprolactone) scaffolds", Tissue Engin. 10(5):673-687 (2004).

Kamil et al., "In vitro tissue engineering to generate a human-sized auricle and nasal tip", Laryngoscope 113:90 (2003).

Kamil et al., "Tissue engineering of a human sized and shaped auricle using a mold", Laryngoscope 114: 867-870 (2004).

Kawazoe et al., "A cell leakproof PLGA-Collagen hybrid scaffold for cartilage tissue engineering", Biotech. Prog. 26 (3):819-826 (2010).

Kim et al., "Cartilage engineered in predetermined shapes employing cell transplantation on synthetic biodegraable polymers", Plast. Reconstr. Surg. 94:233-237 (1994).

Kon et al., "Matrix Assisted Autologous Chondrocyte transplantation for the repair of cartilage defects of the knee: systematic clinical data review and study quality analysis", Am. J. Sports Med. 37:156S (2009).

Kusuhara et al., "Tissue engineering a model for the human ear: assessment of size, shape, morphology, and gene expression following seeding of different chondrocytes", Wound Repair Regen. 17:136-146 (2009).

Liu et al., "In vitro engineering of human ears-shaped cartilage assisted with CAD/CAM technology", Biomats. 31:2176-2183 (2010).

Lotz et al., "Cytotoxic and genotoxic effects of matrices for cartilage tissue engineering", Toxicol. Lett. 190:128-133 (2009).

Neumeister et al., "Vascularized Tissue-Engineered ears", Plast. Reconstr. Surg. 117(1):116-122 (2006).

Park et al., "An update on auricular reconstruction: three major auricular malformation of microtia, prominent ear and cryptotia", Curr. Opin. Otaleryl Head Neck Surg. 18:544-549 (2010).

Rotter et al., "Role for interleukin 1 in the inhibition of chondrogenesis in autologous implants using polyglycolic acid-polylactic acid scaffolds", Tissue Engin. 11(1/2):192-200 (2005).

Rubin J. P. & Yaremchuk M.J., "Complication and toxiticites of implantable biomaterials used in facial reconstructive and aesthetic surgery: a comprehensive review of the literature", Plast. Reconstr. Surg. 100:1336-1353 (1997).

Shieh et al., "Tissue engineering auricular reconstruction: in vitro and in vivo studies", Biomaterials. 25(9):1545-57 (2004).

Sterodimas et al., "Tissue engineering and auricular reconstruction: a review", J. Plast. Reconstr. Aesthet. Surg. 62:447-452 (2009).

Stone et al., "Regeneration of meniscal cartilage with use of a collagen scaffold", J. Bone Joint Surg. Am. 79-A (12):1770-1777 (1997).

Ting et al., "In vitro prefabrication of human cartilage shapes using fibrin glue and human chondrocutes" Ann. Plast. Surg. 40:413-421 (1998).

Tjellstrom, "Osseintegrated implants for replacement of absent or defective ears", Clin. Plast. Surg. 17(2):355-366 (1990).

Vacanti et al., "Tissue engineering growth of new cartilage in the shape of a human ear using synthetic polymers seeded with chondrocytes", 252 Mat. Res. Soc. Symp. Proc. 252:367-374 (1992).

Xu et al., "Tissue-Engineered flexible ear-shaped cartilage", Plast. Reconstr. Surg. 115:1633-1641 (2005).

* cited by examiner

000# ENGINEERED CRANIOFACIAL CONSTRUCTS WITH COMPOSITE SCAFFOLD

CROSS REFERENCE TO RELATED APPLICATIONS

This application claims the benefit of priority of U.S. Provisional Application No. 61/304,926, filed Feb. 16, 2010, incorporated fully herein by reference.

GOVERNMENT SUPPORT

This invention was made with federal government support under contract number W81XWH-08-2-0034, awarded by the Armed Forces Institute of Regenerative Medicine. The U.S. Government has certain rights in the invention.

FIELD OF THE INVENTION

The present invention relates to compositions, devices, and methods useful for reconstructing cartilaginous structures in the craniofacial area including auricular and nasal reconstruction.

BACKGROUND

Reconstruction of the external ear is one of the most challenging problems in plastic surgery because of the complex, three-dimensional properties of the auricular cartilage and overlying skin. Auricular reconstruction may benefit patients with congenital deformities and those injured in accidents or battle, but in the latter instances auricle reconstruction is often aggravated by the complexity of sustained injuries such as severe local skin damage or excessive scarring related to trauma or burns. Current clinical approaches often provide suboptimal aesthetic outcomes.

Autogenous cartilage (engineered cartilage composed of a patient's own cells) has become a feasible option for auricular reconstruction. Unfortunately, distortion and shrinkage of ear-shaped grafts or implants during scaffold degradation and lack of neocartilage maturation in vivo have hindered progress in the field. Scaffolds made of synthetic polymers often generate degradation products that cause an inflammatory reaction and negatively affect neocartilage formation in vivo. Porous collagen, a natural material, is a promising candidate; but without additional support it can not withstand the insidious contractile forces exerted by overlying soft tissue during normal wound healing. Hence, there remains a need in the art for stable, biocompatible scaffold materials and approaches to ear reconstruction that maintain the complex three-dimensional structure over the long term.

SUMMARY

Aspects of the present invention provide for a construct for craniofacial cartilage reconstruction, comprising a permanent, shape memory support embedded into a shaped porous scaffold. This composition maintains the implant's size and specific three-dimensional shape, and allows elastic deformation and return to original (pre-deformed) ear shape. More specifically, human adult ear-shaped fibrous collagen scaffolds with embedded a coiled titanium wire were seeded with chondrocytes or mesenchymal stem cells, cultured in vitro for up to 12 weeks, and implanted into animal subjects. The dimensional changes in all wire-containing implants were minimal. No gross distortion occurred over the in vivo study period. There were no adverse effects on neocartilage formation from the embedded wire. Histologically, mature neocartilage extracellular matrix was observed throughout all implants, demonstrating robust autologous cartilage formation on porous, fibrous collagen scaffolds. The amount of DNA, glycosaminoglycan, and hydroxyproline in the engineered cartilage were similar to that of native ear cartilage. The embedded wire support prevented shrinkage of the ear-shaped porous collagen constructs.

An embodiment of the present invention provides for a composition for auricular reconstruction comprising a biocompatible porous scaffold designed with an auricular shape, and a permanent framework within the scaffold, wherein the permanent framework is flexible, resilient, and maintains the auricular shape of the scaffold. The framework can be a wire framework comprising a central wire and a wire coil surrounding it, wherein the central wire has the shape of the prominent ear features and the surrounding coil provides surface area and loops for tissue integration. The composition may further comprise viable cells. The composition may further comprise cartilage. In a particular embodiment, the composition comprises an ear-shaped fibrous collagen scaffold supported by a titanium wire framework and populated with chondrocytes or mesenchymal stem cells. In a still more particular embodiment, the composition comprises an ear-shaped fibrous collagen scaffold supported by a titanium wire framework, further comprising cells and cartilage. The scaffold may further comprise an active biomolecule agent.

Another embodiment provides for a method of making an implant for auricular reconstruction comprising obtaining a mold of an ear, casting into the mold a porous biocompatible scaffold material in which a metal framework is embedded, and releasing the ear-shaped scaffold material from the mold to obtain a frame-work supported auricular implant. The scaffold material can be seeded with viable cells, either before, during, or after the casting step. The framework supported auricular implant can be incubated so that the viable cells infiltrate the implant; and can be incubated for a period of time sufficient for cartilage to form within the implant.

Yet another embodiment provides for a method of auricular reconstruction comprising obtaining a mold of an ear, casting into the mold a porous biocompatible scaffold material in which a metal framework is embedded, releasing the scaffold material from the mold to obtain an ear-shaped, framework-supported auricular implant, seeding the auricular implant with viable cells, incubating the auricular implant to allow the cells to grow and form cartilage, and implanting the auricular implant under the skin of a subject. The implant can be subsequently explanted and reimplanted at another site. The subject may be an animal or a human.

DESCRIPTION OF THE DRAWINGS

The application file contains at least one drawing executed in color. Copies of this patent application publication with color drawing(s) will be provided by the Office upon request and payment of the necessary fee.

FIG. 3A-3D: constructs with wires, FIGS. 3E-3H: constructs without wires. The construct size was maintained in scaffolds with wires (3D) but was not maintained in scaffolds without wires (3H) after 2 weeks in vitro culture.

FIGS. 6A-6D: constructs with wire supports; FIGS. 6E-6H: constructs without wire supports; FIGS. 6I-6L, native sheep ear cartilage. Staining: 6A, 6E, 6I with hematoxylin and eosin (H&E); 6B, 6F, 6J stained with safranin-O; 6C, 6G, 6K stained with toluidine blue; 6D, 6H, 6L stained with Verhoeff's elastin stain. Residual collagen fibers of the scaffold stained red on H&E and elastin-stained slides and green on safranin-O-stained slides. Scale bar 100 μm.

DETAILED DESCRIPTION

Figure 1:
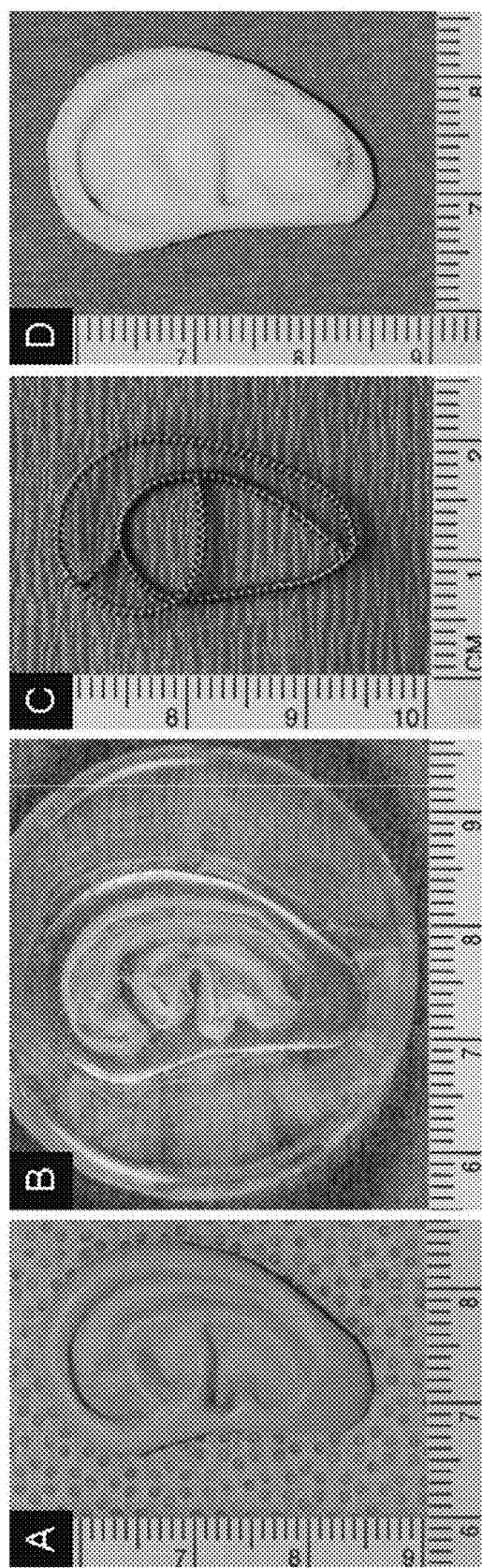
FIG. 1 shows an embodiment of the invention in which a half size human adult ear master was carved by hand in clay (1A) and used to create polydimethylsiloxane molds (1B). Titanium wire frameworks (1C) were bent to simulate the ridges of human auricle. Porous human ear-shaped scaffolds with or without metal frameworks were manufactured from bovine fibrous collagen (1D).

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The present invention provides for compositions, devices, and methods useful for craniofacial (e.g., auricular) reconstruction. Current approaches for complete auricular reconstruction, including carved autologous rib cartilage and alloplastic implants, are prone to complications and often result in suboptimal aesthetic outcomes. Bauer et al., 124 Past. Reconstr. Surg. 14e (2009). The shortcomings of available auricular implant options stimulated a search for alternative strategies. The ideal auricular implant would have low extrusion rates, remodel, and heal after trauma. Tissue engineered cartilage, derived from autologous cells combined with biodegradable scaffold material, has the potential to meet these requirements; cartilage engineered from chondrocytes suspended in hydrogels or seeded onto resorbable scaffolds has been demonstrated in vitro and in vivo. Kim et al., 94 Plast. Reconstr. Surg. 233 (1994); Chung et al., 77 J. Biomed. Mat. Res. A 518 (2006).

The current difficulties related to engineering human ear-shaped cartilage, with its associated complex architecture and largely unsupported, protruding, three-dimensional structure, have been reported. Vacanti et al., 252 Mat. Res. Soc. Symp. Proc. 367 (1992); Cao et al., 100 Plast. Reconstr. Surg. 297 (1997); Xu et al., 115 Plast. Reconstr. Surg. 1633 (2005); Kusuhara et al., 17 Wound Repair Regen. 136 (2009); Neumeister et al., 117 Plast. Reconstr. Surg. 116 (2006); Isogai et al., 74 J. Biomed. Mat. Res. A 408 (2005); Isogai et al., 10 Tissue Engin. 673 (2004); Kamil et al., 113 Laryngoscope 90 (2003); Haisch et al., 259 Otorhinolaryngol. 316 (2002).

The challenge remains to demonstrate specific shape retention of the auricle in longer term in vivo studies. Shape changes inevitably occurred upon degradation of the internal supporting polymer scaffold (Shieh et al., 2004; Isogai et al., 2004), or removal of external stents, which were preserving auricle shape (Cao et al., 1997; Xu et al., 2005; Neumeister et al., 2006).

The success of engineering auricular cartilage largely depends upon the ability of the scaffold to: support cartilage formation, withstand contractile healing forces, and degrade without deleterious effects on the newly formed tissue. To maintain implant structural integrity in the presence of immature developing tissue, the supporting scaffold must withstand the insidious healing forces encountered upon subcutaneous implantation, especially in an immunocompetent animal model. The degradation rate of the scaffold material must approximate the rate of new tissue formation; premature degradation leads to scaffold collapse and loss of implant shape.

Prior experimental auricle scaffolds have often been manufactured from a combination of polyglycolic acid (PGA), poly-L-lactic acid (PLLA), polycaprolactone (PCL), and porous poly(vinyl alcohol)-alginate. Kim et al., 1994; Vacanti et al., 1992; Cao et al., 1997; Shieh et al., 2004; Kusuhara et al., 2009; Isogai et al., 2005; Isogai et al., 2004; Haisch et al., 2002; Liu et al., 2010; Bichara et al., 163 J. Surg. Res. 331 (2010). Mechanical properties and degradation rates of synthetic materials can be modified and polymers can be combined in various ratios to meet the mechanical and degradation requirements discussed above. Indeed, the ear-shaped constructs containing polymers with slower degradation rates, such as PCL, were better preserved at the end of the studies because the shape of the auricle was maintained mostly by the still present scaffold material. Shieh et al., 2004; Kusuhara et al., 2009; Isogai et al., 2005; Isogai et al., 2004. Unfortunately, the degradation products of the synthetic materials usually trigger chronic inflammation that can negatively affect neocartilage formation. Fujihara et al., 31 Biomats. 1227 (2010); Hsu et al., 30 Artif. Organs 42 (2006); Lotz et al., 190 Toxicol. Lett. 128 (2009); Rotter et al., 11 Tissue Engin. 192 (2005).

Natural materials, such as collagen, are promising candidates for cartilage engineering; being part of extracellular matrix (ECM), natural materials are abundant and biocompatible and their use eliminates the negative impact of the degrading synthetic polymers on neocartilage. Parenteau-Bareil et al., 3 Mats. 1863 (2010); Glowacki & Mizuno, 89 Biopolymers 338 (2008). Although significant immune response can be mounted to collagen-based products, advances in collagen purification and processing have rendered them biocompatible. Lyn et al., 71 J. Biomed. Mat. Res. B Appl. Biomat. 343 (2004). Scaffolds made of collagen originating from diverse animal tissues are commercially available and have been actively used in research and clinical applications. Employing collagen scaffolds, several types of tissues, including meniscal cartilage, have been successfully regenerated (Stone et al., 79 J. Bone Joint Surg. Am. 1779 (1997), and osteochondral defects have been repaired in patients (Steinwachs & Kreuz, 23 Arthroscopy 381 (2007); Kon et al., 37 Am. J. Sports Med. 156S (2009).

In studies described herein, cartilage formation from sheep auricular chondrocytes cultured in vitro on fibrous collagen (type I collagen originating from bovine dermis, Kensey Nash Corp., Exton, Pa.) scaffolds using various methods and for varying times prior to implantation were evaluated in models such as nude mice, rats, and sheep. Robust neocartilage formation was demonstrated in all study groups after 6 weeks in vivo. Unfortunately, fibrous collagen is mechanically weak and lacks the strength to withstand contractile forces exerted by skin and overlying soft tissue during healing.

Figure 2:
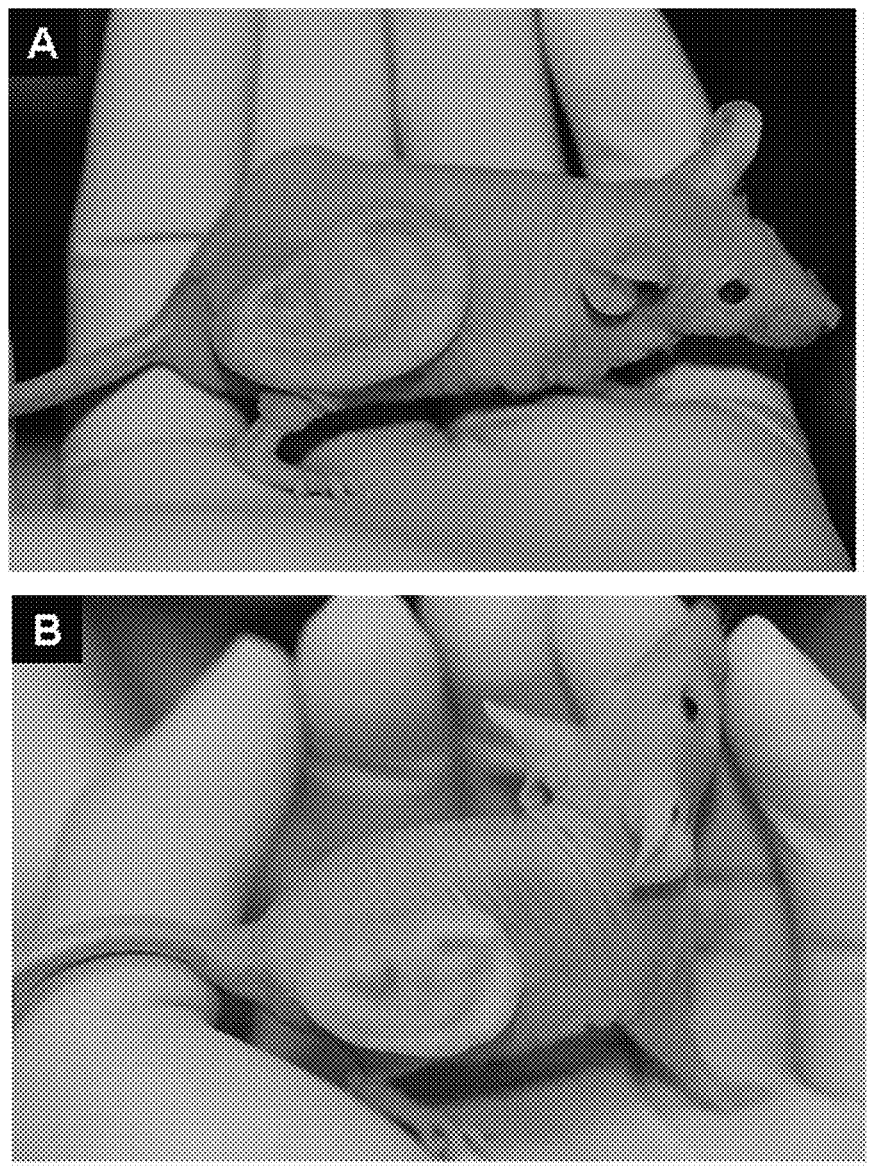
FIG. 2 compares human ear-shaped constructs (2A) with and (2B) without internal wire support on the backs of nude mice. The constructs retained characteristic ear shape at 6 weeks.
Figure 3:
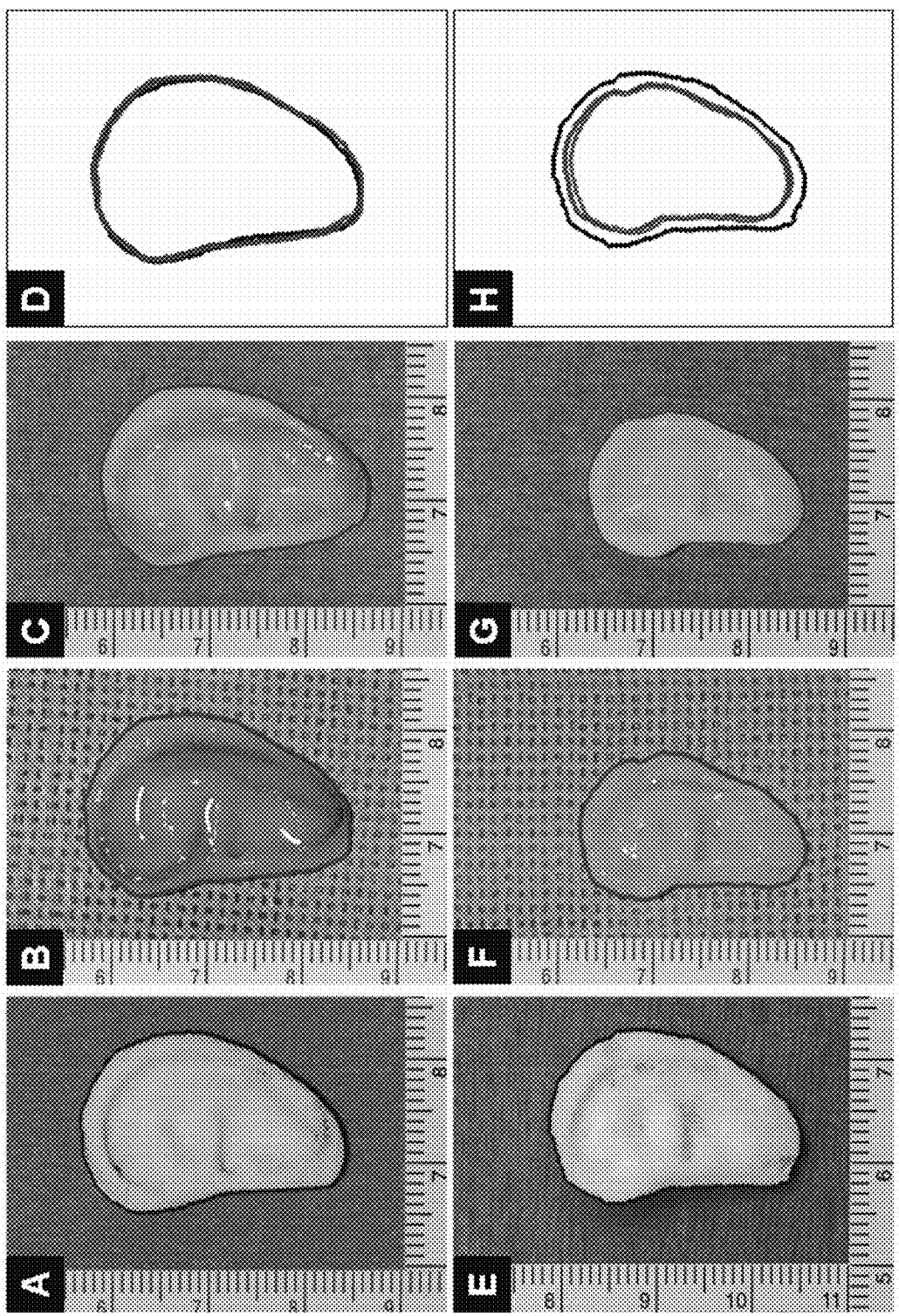
FIG. 3 provides gross images of example ear-shaped constructs. (3A) and (3E): before cell seeding; (3B) and (3F): after 2 weeks of in vitro pre-culture; (3C) and (3G): after 6 weeks in vivo; (3D) and (3H): comparison of sizes at different stages.
Figure 9:
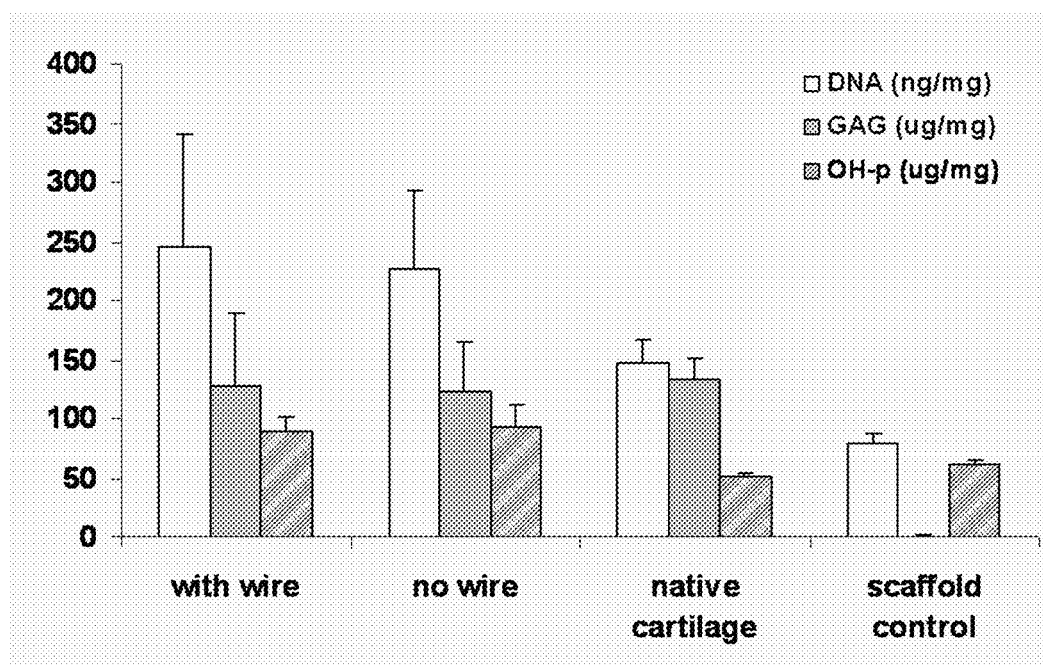
FIG. 9 presents data of DNA, glycosaminoglycan (GAG) and hydroxyproline (OH-proline) content. Data are presented as mean±standard deviation. DNA is presented as ηg/mg construct wet weight, GAG and OH-proline as μg/mg construct dry weight.

In some embodiments of the present invention, a permanent framework, e.g., a coiled titanium wire framework, was embedded within a matrix, e.g., a collagen scaffold, to maintain the size and ear-like shape of the construct during neocartilage formation, scaffold remodelling, and exposure to wound healing forces. Gross evaluation showed that all animals survived until the predetermined endpoints; no extrusion of constructs or wire supports was observed during the study period. All implants maintained their original shape and resembled a human-shaped ear (FIGS. 2, 3 and 9). The development of cartilage in the scaffold, particularly in scaffolds incubated in vitro for sufficient time for cartilage formation prior to implantation, appeared advantageous. Without being bound by theory, it appears that the cartilage provides protection from the host's immune response, which may occur to some extent even when the scaffold includes autologous cells.

Figure 4:
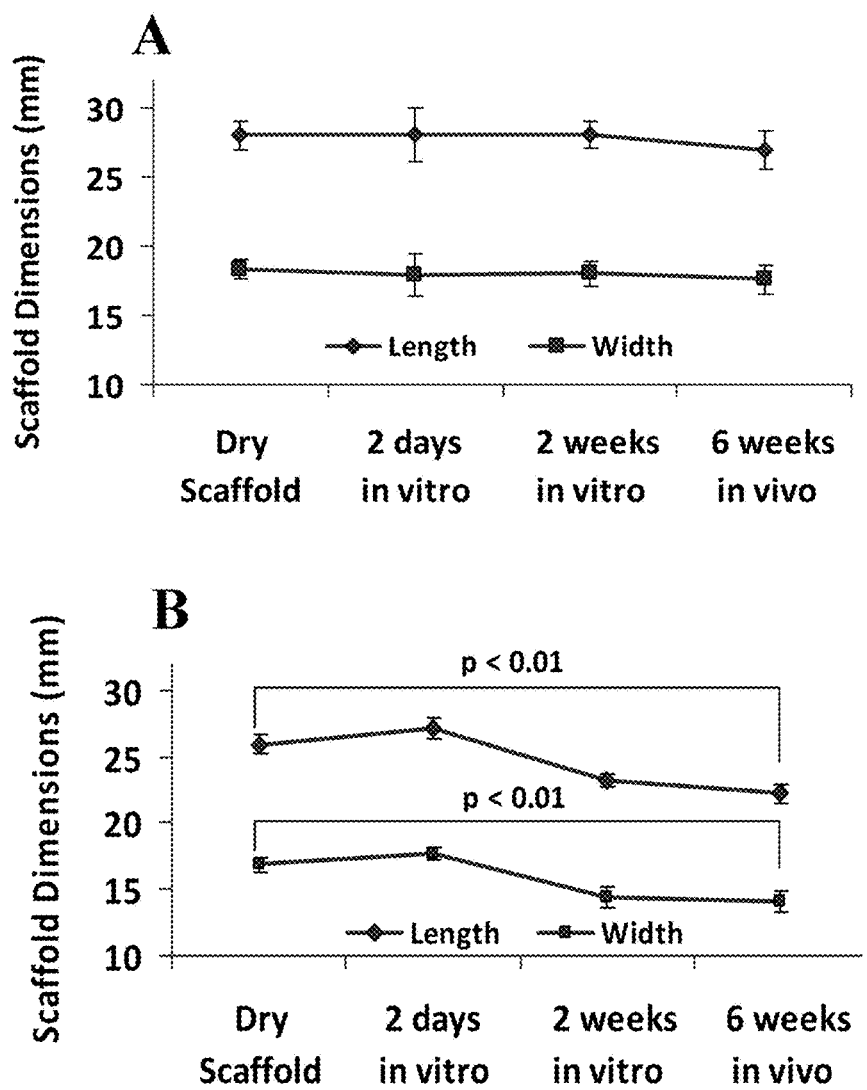
FIG. 4 shows construct size changes during an experiment. The length and width of the scaffolds containing wire supports, shown in (4A) did not change. Scaffolds without wire supports, shown in (4B) decreased in size after initial swelling at 2 days and significantly decreased in size and remained smaller after 2 weeks in vitro culture and after 6 weeks in vivo.

During the 2-week in vitro culture of some embodiments, the constructs with wire support maintained their size while the constructs without wire support decreased in both length and width (FIG. 3). There was no considerable change in dimensions of either construct type during the 2 weeks in vivo. Construct size changes during the experiment are presented in FIG. 4. Significantly less dimensional changes were observed in ear-shaped constructs with wire support than in constructs without wire support (p<0.05). No significant changes in length or width were found in constructs with internal wire support (2.0% length and 4.1% width). Constructs without wire support initially swelled at 2 days in vitro but both dimensions decreased and remained smaller at the 6 week in vivo time point (14.4% length and 16.5% width).

Figure 5:
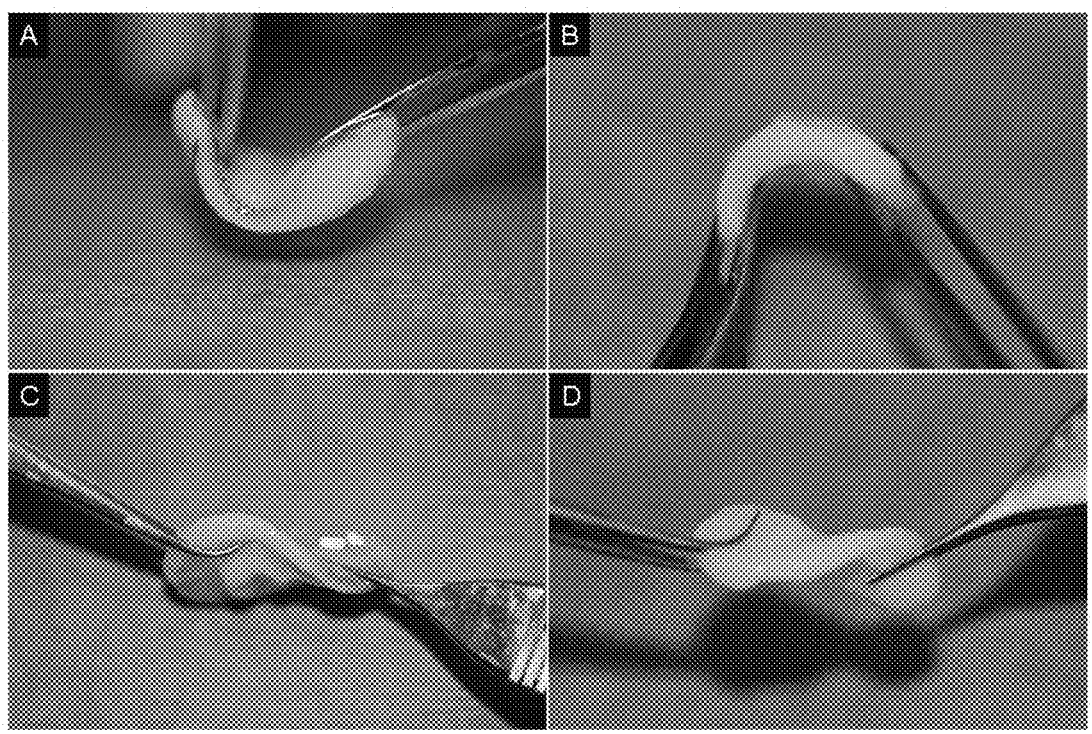
FIG. 5 evidences the bending and torsional flexibility of ear-shaped constructs with internal wire support (5A and 5C) and without wire support (5B and 5D) after 6 weeks in vivo.

At 6 weeks post-implantation into athymic mice, all constructs were surrounded by a thin, fibrous capsule that could be removed easily. Grossly, the tissue resembled cartilage and all ear-shaped constructs, both with and without internal wire support, were flexible (FIG. 5). Similar results were observed in nude rats at 5 weeks post-implantation.

Figure 6:
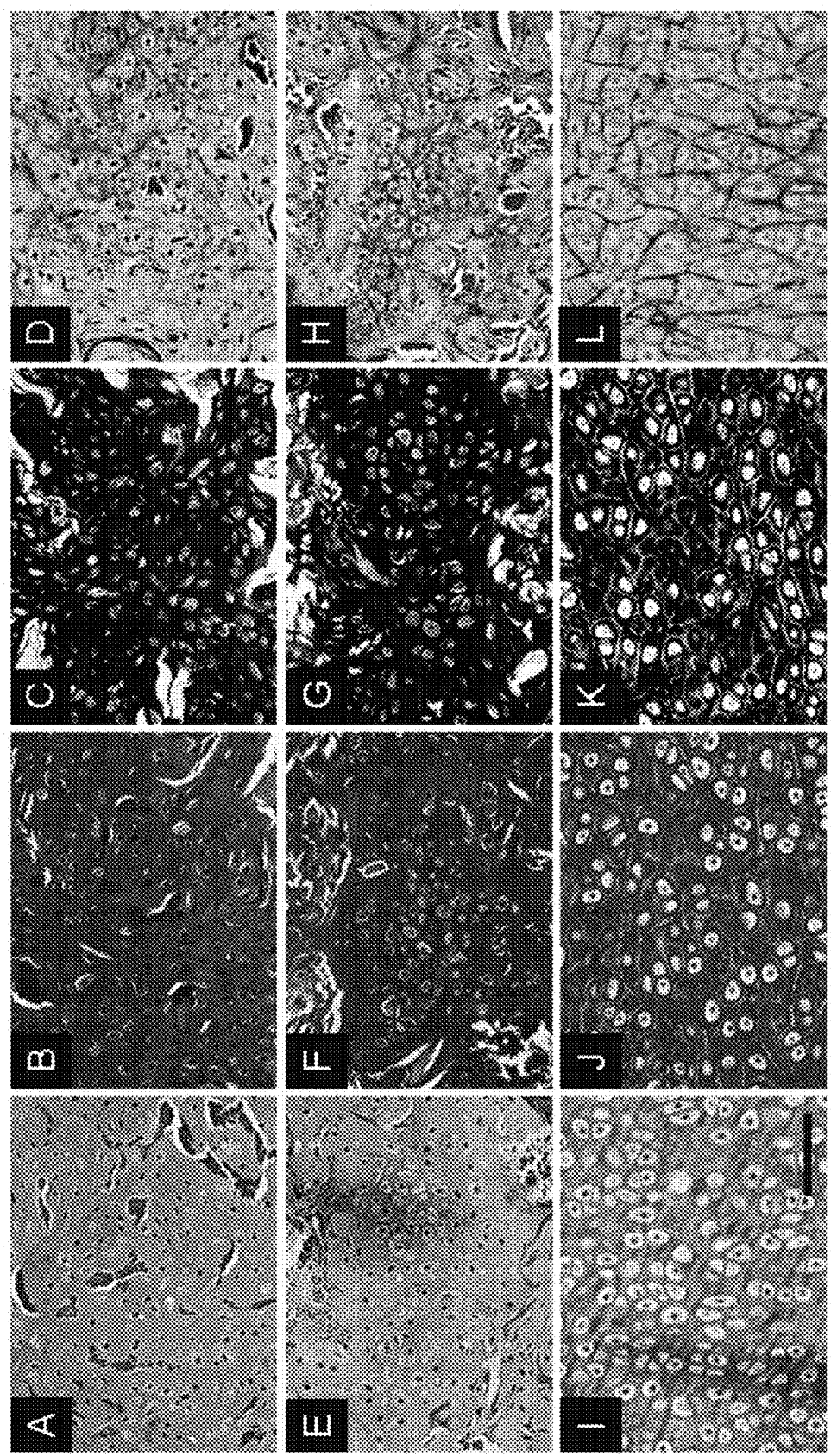
FIG. 6 presents evidence that the histological appearance of engineered cartilage after 6 weeks in vivo was similar to that of native sheep ear cartilage.
Figure 11:
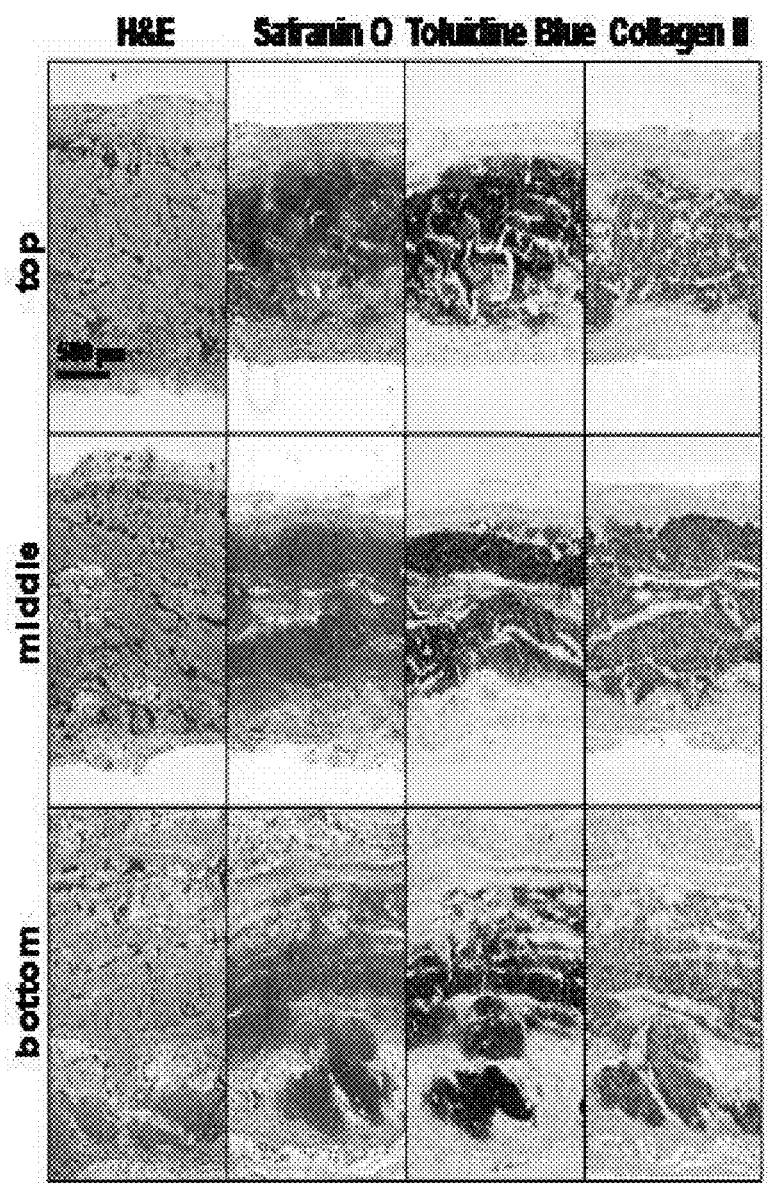
FIG. 11 provides histology data of neocartilage formation in the explanted ear of FIG. 10.

The morphology of neocartilage explanted from nude mice was similar in ear-shaped constructs with and without internal wire support (FIG. 6) and similar to that explanted from a nude rat (FIG. 11). The chondrocytes in the newly formed tissue demonstrated similar morphologic characteristics to those seen in native sheep auricular cartilage and were located within evenly distributed ovoid lacunae. Collagen fibers of the scaffold were seen throughout the neocartilage ECM (FIGS. 6A, 6E and 6I). Similarly, the neocartilage ECM, like native cartilage ECM, stained intensely with safranin-O and toluidine blue, indicating the presence of abundant sulfated GAG (FIGS. 6B, 6C, 6F, 6G, 6J, 6K). Weak positive staining for elastin was detected in the engineered cartilage in both types of constructs at the six-week time point (FIGS. 6D and 6H).

Figure 7:
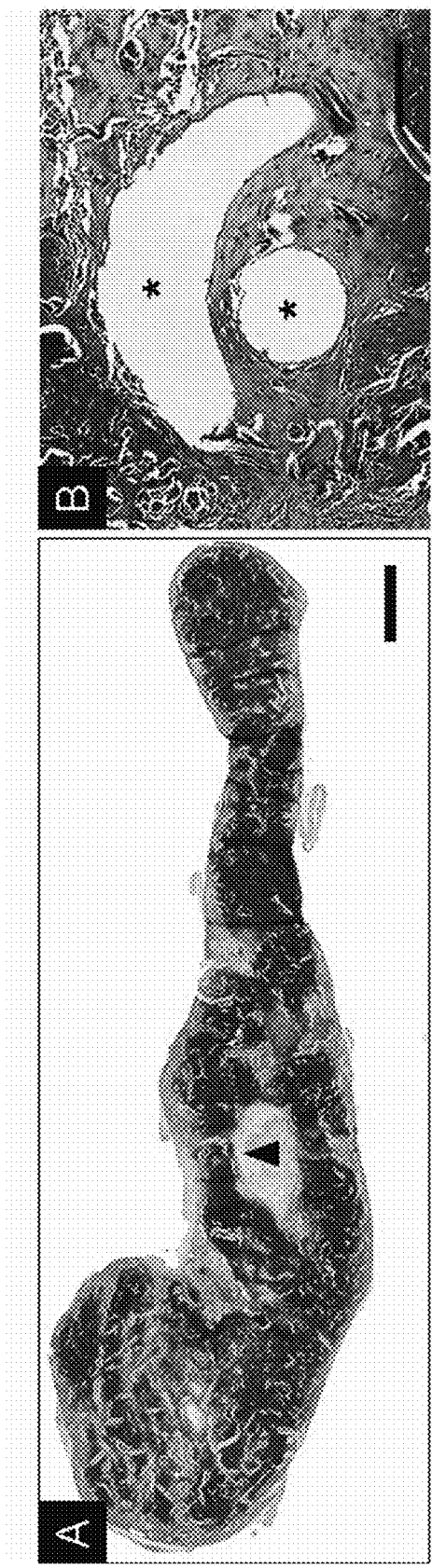
FIG. 7 shows a composite image of the cross section of the ear-shaped construct without wire, demonstrating neo-cartilage formation throughout the construct after 6 weeks in vivo (7A). The small areas in the middle of the construct (arrowhead) did not stain positively for cartilage extracellular matrix (ECM) possibly due to scaffold production artifacts such as uneven distribution of collagen fibers within the scaffold or air bubbles. Neocartilage formation was observed within the rings of the coils of the titanium wire (*) in the scaffolds with internal wire support (7B). Safranin-O staining, scale bars: (7A): 1 mm; (7B): 200 μm.

A composite image of the cross section of the ear-shaped construct without wire (FIG. 7A) demonstrated cartilage ECM formation throughout the construct, as evidenced by safranin-O staining. Small areas in the middle of the construct did not stain positively for cartilage ECM; some of those areas appeared to have densely packed scaffold fibers and low cellularity, some areas contained no scaffold fibers and were filled with loose connective tissue. In the cross section of the ear-shaped construct with wire, neocartilage formation was observed within the rings of the titanium coil of the internal wire support (FIG. 7B).

Figure 8:
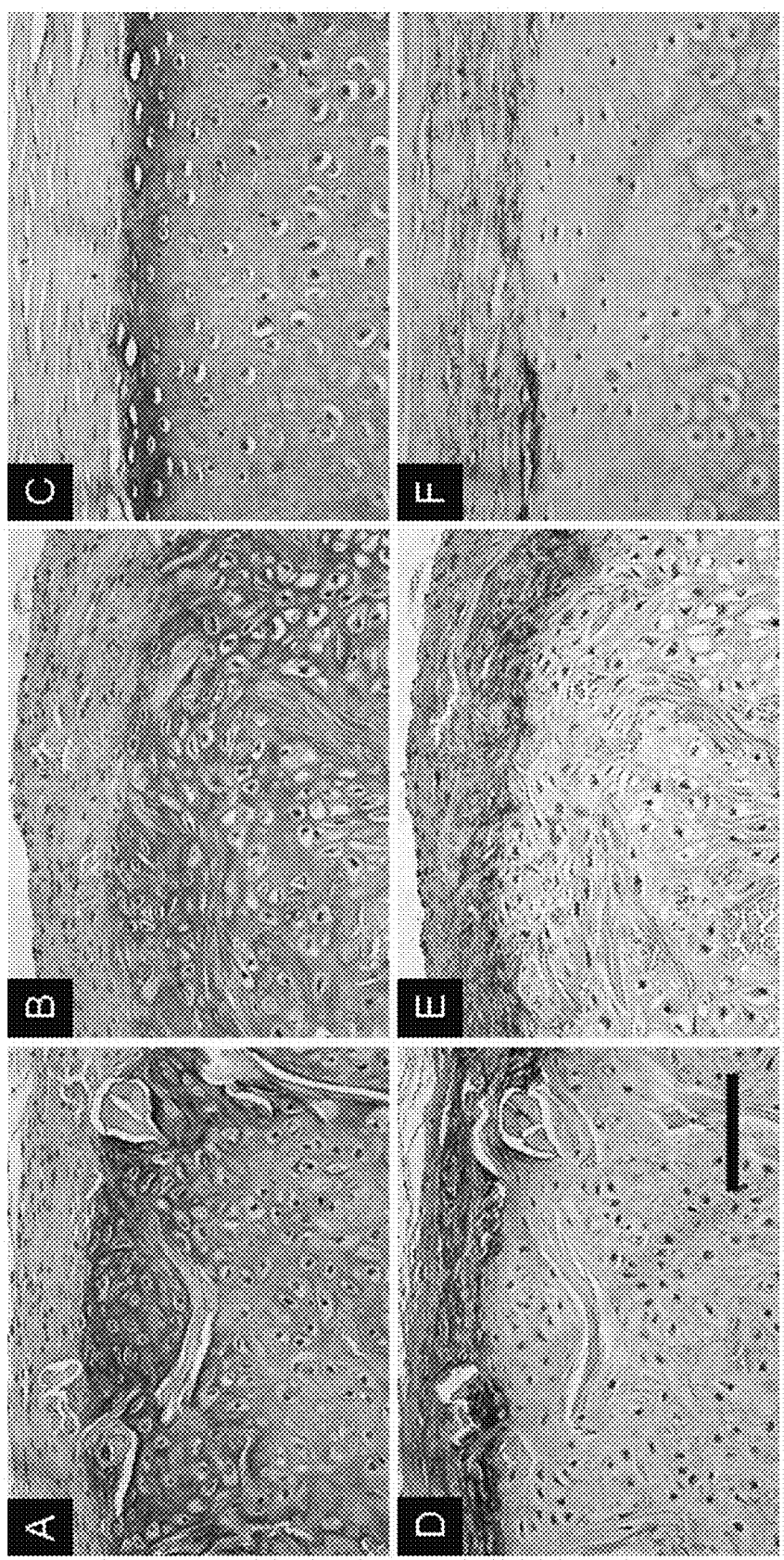
FIG. 8 shows immunohistochemical staining for collagen type II (8A-8C) and type I (8D-8F) of engineered cartilage in the constructs with (8A and 8D) and without wire support (8B and 8E), and of native sheep auricular cartilage (8C and 8F). Positive collagen type II staining (brown) was observed throughout the engineered cartilage, similar to native cartilage, while positive collagen type I staining was seen at the surface in both types of constructs and in the perichondrium of native cartilage. Scale bar, 200 μm.

Immunohistochemical analysis demonstrated cartilage-specific ECM in constructs, with and without wire support, as collagen type II was expressed in the ECM surrounding the chondrocyte ovoid lacunae (FIGS. 8A and 8B). Collagen type II staining was more intense at the periphery and was less intense near the center of the constructs. Collagen type I was expressed at the surface of the both construct types (FIGS. 8D and 8E). These collagen staining patterns are similar to that observed in native sheep ear cartilage (FIGS. 8C and 8F). Collagen fibers of the scaffold (bovine collagen type I) did not stain for collagen type I indicating the lack of species cross reactivity for this antibody.

Quantitative DNA and ECM analyses were also conducted for the ears implanted in nude mice. The DNA content (FIG. 9) of engineered, ear-shaped constructs was similar in constructs with and without wire support (245.4±95.7 and 226.1±67.4 ng/mg wet weight respectively) and similar to that of native sheep ear cartilage (147.2±18.6 ng/mg, p>0.1). The DNA content of the control acellular scaffolds was low (79.1±9.2 ng/mg, p<0.05), and could be attributed to the migration of mouse cells into the scaffold upon implantation. The amount of GAG in the constructs was similar; 127.4±61.5 and 122.1±43.6 μg of GAG/mg dry weight in constructs with and without wire support respectively (p>0.1). The GAG content of engineered cartilage was similar to that of native sheep ear cartilage (133.4±18.1 μg/mg, p>0.1) and no GAG could be detected in the control acellular scaffolds. The amount of OH-proline was 89.5±12.7 and 93.3±19.8 μg/mg dry weight in the constructs with and without wire support respectively (p>0.1). OH-proline content of ear-shaped engineered cartilage, both with and without wire support, was higher than that of the native sheep ear cartilage (50.2±3.4 μg/mg, p<0.05) and the acellular scaffold control (60.7±3.7 μg/mg, p<0.05). The higher amount of OH-proline in the engineered cartilage, as compared to native sheep auricular cartilage, can be attributed in part to the collagen material of scaffold, which has been digested along with the collagen of engineered cartilage ECM and possibly contributed to the overall OH-proline content. In the acellular scaffold control, OH-proline content is attributed mostly to the collagen of the scaffold material. After 6 weeks in vivo, however, no difference was detected between DNA, GAG and OH-proline content of the constructs cultured in vitro for 2 days versus those cultured for 2 weeks prior to implantation in the immunocompromised mice.

Constructs were also implanted in sheep to study cartilage formation in a large, immunocompetent animal model. Grossly, constructs explanted from younger sheep appeared thicker and smaller in diameter than constructs explanted from older animals. This may be due to the inflammatory response that was detected upon histological examination. In older sheep, neocartilage formation was seen throughout the scaffolds and was interrupted by residual scaffold fibers; in younger sheep, cartilage formation was non-contiguous. Minimal inflammatory reaction without foreign body response was seen in older sheep, and the histological picture resembled that seen in corresponding control mice. In sheep, a severe inflammatory and foreign body reaction was observed in response to constructs made with PLA/PCL. Using histology to evaluate neocartilage formation, no difference was detected between the length (2 weeks vs. 6 weeks) and the type of in vitro culture. In control immunocompromised animals, neocartilage formation was observed consistently throughout the scaffolds, including PLA/PCL scaffolds. Minimal inflammatory response and no foreign body reaction were observed.

Multiple efforts to engineer human ear-shaped cartilage have been hindered by the inability to retain the size and shape of the construct for the duration of in vivo studies. Sheih et al., 2004; Kusuhara et al., 2009; Neumeister et al., 2006; Isogai et al., 2004; Ting et al., Ann. Plast. Surg. 413 (1998); Kamil et al., 114 Laryngoscope 867 (2004); Chung & Burdick, 60 Adv. Drug Deliv. Rev. 243 (2008). To preserve the specific shape of a human auricle, many approaches have been investigated, including reinforcement of a scaffold with an additional synthetic polymer PLLA (Vacanti et al., 1992, Cao et al., 1997; Shieh et al., 2004; Kusuhara et al., 2009; Isogai et al., 2005; Kamil et al., 2003; Haisch et al., 2002; Kawazoe et al., 26 Biotech. Prog. 819 (2010)); use of temporary external stents (Cao et al., 1997; Xu et al., 2005; Neumeister et al., 2006); acrylic sheet (Kamil et al., 2003); implantable perforated gold mold (Kamil et al., 2004); and use of wire sutures to support a carved rib framework (Nagata Technique), the latter having a high rate of necrosis and extrusion of cartilage from the wire sutures. See also Rubin & Yaremchuk, 100 Plast. Reconstr. Surg. 1336 (1997); Sterodimas et al., 62 J. Plast. Reconstr. Aesthet. Surg. 447 (2009); Park et al., Curr. Opin. Otaleryl Head Neck Surg. (2010).

The present invention provides for a novel strategy: reinforce the ear-shaped porous collagen scaffold with an internal titanium wire skeleton. In a particular embodiment, a coiled titanium wire, bent to simulate the ridges of a human auricle, was embedded into porous collagen, thereby combining the advantages of the biological nature of collagen material and the mechanical properties of the titanium wire. Titanium has been demonstrated to be a biocompatible material and is used routinely in medical implants for numerous applications including auricular replacement. Tjellström, 17 Clin. Plast. Surg. 355 (1990).

The results presented herein demonstrate that the size and ear-like shape were preserved throughout the experiment in all implants with internal wire support. After the initial swelling, significant reduction in size occurred in constructs made of porous collagen alone; however, the human ear-like shape of the constructs was grossly preserved. The reduction in size occurred after 2 weeks of in vitro culture without any further reduction during subsequent 6 weeks in vivo. The shrinkage is possibly due to the beginning of ECM formation. This finding corroborates the assessment of the Kensey Nash multiphasic composite scaffold for osteochondral defect repair; the authors observed slight contraction of the cell-seeded collagen layer after 3 weeks of in vitro culture. Heymer et al., 3 J. Tissue Engin. Regen. Med. 389 (2009). The lack of further reduction in size during the in vivo period may be attributed to rather loose subcutaneous connective tissue in rodents and the reduced inflammatory response in nude mice as evidenced by the formation of a thin fibrous capsule. In a large animal model, stronger contraction forces are expected to be exerted by skin and surrounding tissue during healing, approximating conditions in humans.

The results presented herein also suggest that the internal wire framework is important for the preservation of the dimensions of the engineered ear during in vitro culture and after implantation into the animal model. Titanium wire was well-incorporated into the neocartilage, without any adverse effects on chondrocyte viability, adhesion to scaffold material, and cartilage ECM formation suggesting low possibility of extrusion in the future. Histologically, there was no difference between neocartilage that formed in the constructs with and without internal wire support. Weak elastin expression was observed in both types of constructs after 6 weeks in vivo, suggesting that elastic cartilage started to form at this early time point.

Any differences between the cartilage that formed in nude mice after 2 days and 2 weeks of in vitro culture prior to implantation were not readily identifiable. In a large animal model, however, in vitro pre-culture may be important to achieve autologous cartilage formation prior to implantation. Such an approach may help reduce the inflammatory and foreign body response that can be induced by a scaffold made from collagen originating from a different species and by antigen-presenting chondrocyte surface in an immunologically active subcutaneous environment. Haisch, 68 Adv. Otorhinolaryngol. 108 (2010). Without being bound by theory, it appears that the cartilage protects the scaffold matrix, and the milieu therein, from the subject's immune response, which may occur to some extent even when the scaffold includes highly processed collagen and autologous cells.

Staining of the cross sections obtained from the ear-shaped implants without wires with safranin-O demonstrated a few areas in the center of the constructs that did not show the presence of cartilage-specific GAG (FIG. 7A). Some of these staining defects appeared to have lower cellularity and may be due to scaffold production artifacts such as uneven distribution of collagen fibers within the scaffold or air bubbles. On the other hand, the thickness of the constructs often exceeded 3 mm which might have negatively affected chondrocyte survival in the central part of the constructs due to limited nutrient and gas diffusion. The design of the ear-shaped scaffold can be modified to reduce the thickness of engineered cartilage so that it more closely resembles human auricular cartilage; this thickness reduction should eliminate this central defect if it is related to construct thickness.

In the present invention, auricular cartilage was engineered and the size of the human ear-like construct was retained because of the presence of the internal titanium wire framework. The embedded wire support was essential to prevent shrinkage of the ear-shaped porous collagen constructs. Engineering human ear-shaped cartilage with preserved dimensions represents an important milestone in efforts to develop a replacement living auricle for patients with congenital and acquired external ear defects, and as a prototype for building other structural elements of the face, such as nose, mandible, and cheek complex. The improved composite scaffold represents a novel, promising approach for future clinical applications and serves as a step in the development of a fully resorbable ear-shaped scaffold.

For ear-shaped constructs, the morphology of the auricle can be designed, for example, by sculpting and mold formation, by CAD/CAM manufacturing (Liu et al., 31 Biomats. 2176 (2010)), or by 3D laser scanning method for shape analysis. Molds can be made of any suitable material, such as steel or polydimethylsiloxane. In one embodiment, human adult ear-shaped fibrous collagen scaffolds with and without embedded coiled titanium wire were seeded with heterologous chondrocytes, cultured in vitro for up to 2 weeks, and implanted in nude mice. After 6 weeks, the dimensional changes in all implants with wire support were minimal (2.0% in length and 4.1% in width), while significant reduction in size occurred in the constructs without embedded wire (14.4% in length and 16.5% in width). No gross distortion occurred over the in vivo study period. There were no adverse effects on neocartilage formation from the embedded wire. Histologically, mature neocartilage extracellular matrix was observed throughout all implants. The amount of DNA, glycosaminoglycan, and hydroxyproline in the engineered cartilage were similar to that of native ear cartilage. The embedded wire support was useful for avoiding shrinkage of the ear-shaped porous collagen constructs.

The scaffold material should have sufficient porosity to allow the passage of cells and/or cellular material. The scaffold includes at least one biocompatible polymer, such as collagen, chitosan, silk fibroin, cellulose, gelatin, oligosaccharides, starch, pectin, heparin, hyaluronic acid and derivatives thereof, carboxymethylcellulose, porous poly(L-lactide), poly(DL-lactide-co-caprolactone, polyethylene, alginate, amelogenin, pluronic F-127, polyglycolic acid, glycosaminoglycan-synthetic polymer conjugates, or other biocompatible polymers, or mixtures thereof.

The scaffold can be collagen, such as fibrous collagen, type I or type II collagen, or recombinant collagen. The term "collagen" is used in its conventional sense to describe a material which is the major protein component of the extracellular matrix of bone, cartilage, skin, and connective tissue in animals and derivatives. Collagen in its native form is typically a rigid, rod-shaped molecule approximately 300 nm long and 1.5 nm in diameter. It is composed of three collagen polypeptides which form a tight triple helix. The collagen polypeptides are characterized by a long midsection having the repeating sequence -Gly-X-Y-, where X and Y are often proline or hydroxyproline, bounded at each end by the telopeptide regions, which constitute less than about 5% of the molecule. The telopeptide regions of the collagen chains are typically responsible for the crosslinking between chains, and for the immunogenicity of the protein. Collagen occurs in several types, having differing physical properties. The most abundant types are Types I-III. The present disclosure includes these and other known types of collagen including natural collagen and collagen which is processed or modified, i.e., various collagen derivatives. Collagen is typically isolated from natural sources, such as porcine or bovine hide, cartilage, or bones. Bones are usually dried, defatted, crushed, and demineralized to extract collagen, while hide and cartilage are usually minced and digested with proteolytic enzymes (other than collagenase). As collagen is resistant to most proteolytic enzymes, this procedure conveniently serves to remove most of the contaminating protein found with collagen. Collagens (and gelatins) can also be produced using recombinant technology, see, e.g., U.S. Pat. No. 6,992,172; U.S. Pat. No. 6,713,662; U.S. Pat. No. 6,653,450; U.S. Pat. No. 6,617,431. Collagens can be monomerized and cross-linked using biocompatible techniques to form collagen gels, see, e.g., U.S. Pat. No. 6,509,031.

The permanent framework can comprise pure metals or alloys as selected to allow the auricular construct to bend and return to original shape; to be deformed and return to the pre-deformed shape. The metal or alloy should have a good balance of the desired characteristics of strength, resilience and flexibility, which can depend on the metal or alloy itself, or be controlled by the shape and thickness of the framework. The most common metal alloys used in orthopaedic implants are stainless steels, cobalt-chromium alloys, and titanium alloys, which are suitable for the present wire framework. Shape memory alloys can also be used, including copper-zinc-aluminium-nickel, copper-aluminium-nickel, nickel-cobalt-chromium, and nickel-titanium alloys. Titanium alloys are considered to be biocompatible, and are the most flexible of all orthopaedic alloys, and are also lighter weight than most other orthopaedic alloys. Pure titanium wires may also be used. Additionally, tantalum is a pure metal with excellent physical and biological characteristics: it is flexible, corrosion resistant, and biocompatible. The framework may also be made of or include other implantable materials such as Trabecular Metal™ material, which is a strong, flexible, porous biocompatible material made from tantalum over carbon. The framework can include a wire that is bent into the appropriate shape, or it can include a shape memory alloy that is forged into the desired shape. The framework may also comprise polymers such as medical-grade silicone or plastics, such as polyethylene. The framework may be coated with a corresponding hydroxide or other coatings, such as titanium coated with titanium hydroxide. See U.S. Pat. No. 7,410,502, Medical prosthetic devices having improved biocompatibility.

More specifically, an example suitable framework is a wire framework comprising a central wire surrounded by a coiled wire (see FIG. 1C). The central wire is shaped to match the ridges and prominent other ear features, and is designed to withstand the forces experienced after implantation and maintain the scaffold in an ear shape. The surrounding coil is designed to provide additional, and significant, surface area and loops for tissue integration. Tissue integration and encapsulation is important to avoid extrusion of the framework and subsequent loss of the scaffold implant. The coil also provides mechanical strength, which aids in maintaining the ear shape. The central and coiled wire may be separate or contiguous. A suitable wire framework may also be made by braiding or twisting metal wires to achieve sufficient shape, resilience, flexibility, and surface area such that it maintains resiliency and strength in compression so that the framework yields to applied force, yet recovers to nearly its original shape when the force is removed. The framework is shaped and embedded in the scaffold such that after formation of the implant, the entire scaffold can be deformed (compressed, twisted or bent) and upon the release of deforming force considerably or substantially (i.e., to a great extent or degree) recover its original shape.

Additionally, the construct of the present invention can be cultured in vitro to establish a living implant. In this embodiment, the scaffold is combined with cells, such as fibroblasts (Chetty et al., *Hydroxyapatite-coated polyurethane for auricular cartilage replacement: An in vitro study*, 841 J. Biomed. Mats. Res. A 475 (2008)), stem cells (such as mesenchymal stem cells), nerve cells, osteoblasts, and/or chondrocytes. For example, mesenchymal stem cells can be derived from bone marrow or adipose tissue. These cells can be differentiated toward chondrocytes during in vitro culture or in vivo after implantation. Differentiation often requires soluble factors that can be incorporated in culture, and for release in vivo such as described herein. The cells can be autologous (the subject's own), allogeneic or allogenic (same species as the subject), syngeneic (genetically identical or closely related; immunologically compatible so as to allow tissue transplant), xenogeneic or heterologous (derived or obtained from an organism of a different species, as a tissue graft). Chondrocytes can be obtained, for example, from auricular cartilage or other sources such as costal, nasoseptal, and articular cartilage. Thus, the graft can be entirely autologous, homologous, heterologous or alloplastic, or a combination of these.

Additionally, the scaffold can contain at least one active biomolecule agent(s) such as neurotrophins, antioxidants, medications, growth stimulants, stem cells, vasoactive compounds, nucleotides, RNA, DNA, nutrients, cells, nano-robots, antibiotics, antifungals, hormones, anti-seizure medicines, growth hormones.

The biomolecule agent may be a substance such as natural bio-adhesives; recombinant bio-adhesives; natural cell attachment factors; recombinant cell attachment factors; natural biopolymers, recombinant biopolymers; synthetic biopolymers; natural blood proteins, recombinant blood proteins; natural enzymes; recombinant enzymes; natural extracellular matrix proteins; recombinant extracellular matrix proteins; natural extracellular matrix bio-molecules; synthetic extracellular matrix biomolecules; natural growth factors; recombinant growth factors; natural hormones; recombinant hormones; natural peptide hormones; recombinant peptide hormones; synthetic peptide hormones; natural deoxyribonucleic acids; recombinant deoxyribonucleic acids; synthetic deoxyribonucleic acids; natural ribonucleic acids; recombinant ribonucleic acids; synthetic ribonucleic acids; natural receptors; recombinant receptors; enzyme inhibitors; drugs; biologically active anions; biologically active cations; vitamins; adenosine monophosphate (AMP), adenosine diphosphate (ADP); adenosine triphosphate (ATP); marker biomolecules; amino acids; fat acids; nucleotides (RNA and DNA bases); or sugars. The biomolecules can be dispersed throughout the scaffold, or be deposited is an area of the scaffold where a particular bioactivity is desired. The bioactive molecules can be purified from natural sources, or be recombinant or synthetic versions.

Bioactive molecules may also be selected based upon function. For example one might require biomolecules that stimulate bone healing or wound healing, or focus upon biomolecules for stimulating mineral deposition, biomolecules that stimulate cell attachment or proliferation, biomolecules that promote cell differentiation, biomolecules that stimulate bone attachment, biomolecules that stimulate osteoblastic cell proliferation, biomolecules that stimulate differentiation to chondrocytes, biomolecules that stimulate cartilage formation, and/or biomolecules that stimulate osteoblastic cell differentiation. See, e.g., Hwang et al., 212 J. Cell Physiol. 581 (2007). Further examples of bioactive molecules include TGFs, BMPs, amelogenin, ameloblastin, VEGFs, PDGF, HGF, KGF, FGF, polyprolines, collagens, extracellular matrix biomolecules, CD molecules, integrins, RGD-peptides, growth factors, IL-6, osteocalin, osteoprotegrin, BSP, and cytokines.

Example bioactive extracellular proteins and biomolecules include Ameloblastin; amelin; amelogenins; collagens (I to XII); dentin-sialo-protein (DSP); dentin-sialophospho-protein (DSPP); elastins; fibrins; fibronectins; keratins (1 to 20); laminins; tuftelin; carbohydrates; chondroitin sulphate; heparan sulphate; heparin sulphate; hyaluronic acid; lipids and fatty acids; and lipopolysaccarides.

Growth factors and hormones may be included, for example, to promote cell growth, release of other molecules (e.g. extracellular matrix molecules or sugar), cell differentiation and maturation, regulation of metabolic rate, etc. Typical examples of such biomolecules include Activins (Act); Amphiregulin (AR); Angiopoietins (Ang 1 to 4); Apo3 (a weak apoptosis inducer also known as TWEAK, DR3, WSL-1, TRAMP or LARD); Betacellulin (BTC); Basic Fibroblast Growth Factor (bFGF, FGF-b); Acidic Fibroblast Growth Factor (aFGF, FGF-a); 4-1BB Ligand; Brain-derived Neurotrophic Factor (BDNF); Breast and Kidney derived Bolokine (BRAK); Bone Morphogenic Proteins (BMPs); B-Lymphocyte Chemoattractant/B cell Attracting Chemokine 1 (BLC/BCA-1); CD27L (CD27 ligand); CD30L (CD30 ligand); CD40L (CD40 ligand); A Proliferation-inducing Ligand (APRIL); Cardiotrophin-1 (CT-1); Ciliary Neurotrophic Factor (CNTF); Connective Tissue Growth Factor (CTGF); Cytokines; 6-cysteine Chemokine (6Ckine); Epidermal Growth Factors (EGFs); Eotaxin (Eot); Epithelial Cell-derived Neutrophil Activating Protein 78 (ENA-78); Erythropoietin (Epo); Fibroblast Growth Factors (FGF 3 to 19); Fractalkine; Glial-derived Neurotrophic Factors (GDNFs); Glucocorticoid-induced TNF Receptor Ligand (GITRL); Granulocyte Colony Stimulating Factor (G-CSF); Granulocyte Macrophage Colony Stimulating Factor (GM-CSF); Granulocyte Chemotactic Proteins (GCPs); Growth Hormone (GH); 1-309; Growth Related Oncogene (GRO); Inhibins (Inh); Interferon-inducible T-cell Alpha Chemoattractant (I-TAC); Fas Ligand (FasL); Heregulins (HRGs); Heparin-Binding Epidermal Growth Factor-Like Growth Factor (HB-EGF); fms-like Tyrosine Kinase 3 Ligand (Flt-3L); Hemofiltrate CC Chemokines (HCC-1 to 4); Hepatocyte Growth Factor (HGF); Insulin; Insulin-like Growth Factors (IGF 1 and 2); Interferon-gamma Inducible Protein 10 (IP-10); Interleukins (IL 1 to 18); Interferon-gamma (IFN-gamma); Keratinocyte Growth Factor (KGF); Keratinocyte Growth Factor-2 (FGF-10); Leptin (OB); Leukemia Inhibitory Factor (LIF); Lymphotoxin Beta (LT-B); Lymphotactin (LTN); Macrophage-Colony Stimulating Factor (M-CSF); Macrophage-derived Chemokine (MDC); Macrophage Stimulating Protein (MSP); Macrophage Inflammatory Proteins (MIPs); Midkine (MK); Monocyte Chemoattractant Proteins (MCP-1 to 4); Monokine Induced by IFN-gamma (MIG); MSX 1; MSX 2; Mullerian Inhibiting Substance (MIS); Myeloid Progenitor Inhibitory Factor 1 (MPIF-1); Nerve Growth Factor (NGF); Neurotrophins (NTs); Neutrophil Activating Peptide 2 (NAP-2); Oncostatin M (OSM); Osteocalcin; OP-1; Osteopontin; OX40 Ligand; Platelet derived Growth Factors (PDGF aa, ab and bb); Platelet Factor 4 (PF4); Pleiotrophin (PTN); Pulmonary and Activation-regulated Chemokine (PARC); Regulated on Activation, Normal T-cell Expressed and Secreted (RANTES); Sensory and Motor Neuron-derived Factor (SMDF); Small Inducible Cytokine Subfamily A Member 26 (SCYA26); Stem Cell Factor (SCF); Stromal Cell Derived Factor 1 (SDF-1); Thymus and Activation-regulated Chemokine (TARC); Thymus Expressed Chemokine (TECK); TNF and ApoL-related Leukocyte-expressed Ligand-1 (TALL-1); TNF-related Apoptosis Inducing Ligand (TRAIL); TNF-related Activation Induced Cytokine (TRANCE); Lymphotoxin Inducible Expression and Competes with HSV Glycoprotein D for HVEM T-lymphocyte receptor (LIGHT); Placenta Growth Factor (PIGF); Thrombopoietin (Tpo); Transforming Growth Factors (TGF alpha, TGF beta 1, TGF beta 2); Tumor Necrosis Factors (TNF alpha and beta); Vascular Endothelial Growth Factors (VEGF-A, B, C and D); and calcitonins.

Similarly, receptors that bind signaling molecules (e.g., hormone ligands and growth factors) and transmit the signal into the internal machinery of cells may be included. Additionally, receptors typically bind their ligand in a reversible manner, making them suitable as carriers of growth factors that are to be released into the tissue. Thus, scaffolds can be loaded with growth factor receptors, with or without their principal ligands. Examples of suitable receptors with potential for use as bioactive coating on metal hydroxide-coated implants includes: The CD class of receptors CD; EGF receptors; FGF receptors; Fibronectin receptor (VLA-5); Growth Factor receptor, IGF Binding Proteins (IGFBP 1 to 4); Integrins (including VLA 1-4); Laminin receptor; PDGF receptors; Transforming Growth Factor alpha and beta receptors; BMP receptors; Fas; Vascular Endothelial Growth Factor receptor (Flt-1); Vitronectin receptor. Growth factors and/or their receptors can be recombinant, synthetic, or purified from natural sources.

Other drugs can be included in the scaffold for local effects, such as improving local resistance against invading microbes, local pain control, local inhibition of prostaglandin synthesis; local inflammation regulation, local induction of biomineralization and local stimulation of tissue growth. Examples of drugs suitable for incorporation into metal hydroxide layers include: Antibiotics; cyclooxygenase inhibitors; hormones; inflammation inhibitors; NSAID's (non-steroid antiinflammatory agents); painkillers; prostaglandin synthesis inhibitors; steroids, tetracycline (also as biomineralizing agent).

An embodiment of the present invention provides for a method of making a auricular construct for a human, comprising performing a 3D scan of the subject's unaffected ear, or if they don't have one, obtain a scan from someone else; importing the 3D digital shape of the ear into a 3D CAD or modeling program on a computer; modifying the 3D digital file to enhance key features of the ear and remove excess sections to create the desired scaffold shape or form; using the modified digital file, manufacture a mold of the 3D shape. This can be done by either making a positive of the digital file by traditional machining or rapid prototyping, and then casting it in a material which can then be used as a mold. Alternatively, a negative of the file can be machined or rapid prototyped and directly used; designing a metallic wire skeleton to match the 3D digital file so it can fit within the mold; placing the wire skeleton inside the mold; adding a collagen matrix to the mold to create the scaffold; and sterilizing the scaffold.

The constructs can be permanently implanted under the skin of a subject, or under a pedicled flap with a skin graft placed over the pedicled flap. If the auricular implant is placed at the site of the native ear, laser hair removal of scalp flaps may be done prior to reconstruction. Additional skin may be obtained by graft or by the prior placement of tissue expanders. Alternatively, the area of initial implantation need not be the final site of the ear, e.g., the construct may be implanted under an area of relatively soft and hairless skin, such as the inside of the arm, such that skin tissue adheres to the implant and conforms to the ear shape. Tissue expanders can be used to systematically expand the skin, and once sufficient skin has formed, the implant may be moved to the side of the head. Those of ordinary skill in the art of reconstructive surgery are familiar with numerous techniques that address implantation and complications.

In the present invention, auricular cartilage was engineered and the shape and size of the human ear-like construct was retained with the help of the internal titanium wire framework. The embedded wire support allowed for sufficient bending and structural support for avoiding shrinkage of the ear-shaped porous collagen constructs. Engineering human cartilage-containing craniofacial structures with preserved dimensions represents an important milestone in efforts to develop replacement living implants for patients with congenital and acquired external defects. The improved composite scaffold is a viable asset for clinical applications.

EXAMPLES

Example 1. Ear-Shaped Scaffold Design and Manufacture

The wire skeleton structure is comprised of two components: a central wire and a coil surrounding it. The central wire is designed to have the shape of the prominent ear features. It is also designed to withstand the forces experienced after implantation and maintain the scaffold in an ear shape. The surrounding coil is designed to provide additional significant surface area and loops for tissue integration. Tissue integration and encapsulation is necessary to avoid extrusion of the metallic skeleton and subsequent loss of the scaffold implant. The coil also provides mechanical strength which aids in maintaining the ear shape. Currently both components are made from titanium 6AL 4V ELI, but could potentially be made from other materials including gold, titanium alloy, stainless steel, nickel alloy, cobalt chromium, and tantalum.

The central wire of the skeleton could be manufactured by hand or on a CNC wire bending machine. The coil can be manufactured by hand or on a spring coil machine. Once both parts are created they would then have to be assembled, probably by hand. Depending on the materials involved, it could require an additional thermal treatment to define a shape memory, before or after assembly of metal parts.

A bendable, permanent framework was designed using titanium 6AL 4V ELI wire having a diameter of between 0.25 mm to 0.38 mm. In theory, framework diameter can be designed to range between 0.025 mm to 1.25 mm, depending on the material used for the framework. The wire was shaped into an outer coil having a diameter of between 1 mm and 1.5 mm, but the range that could be used includes from 0.5 mm to about 2.5 mm depending on the materials. Coils were manufactured to have a spacing between each wrap of the coil between 0.75 mm and 1.25 mm, but could be made having spacing between each wrap of between 0.25 mm and 2 mm.

Human ear-shaped scaffolds were fabricated for implantation on the back of a mouse. A single half size human adult ear master (28.2 mm×18.4 mm) was carved by hand in clay and used to create polydimethylsiloxane molds. Metal frameworks bent to mimic the shape of the human ear were made of 0.25 mm diameter coiled titanium wire (Small Parts Inc., Logansport, Ind.). Composite metal and collagen (low density, fibrous bovine dermis-derived type I collagen) ear-shaped scaffolds were manufactured by Kensey Nash Corp. (Exton, Pa.) (FIG. 1). Metal frameworks were embedded in half of the collagen scaffolds; the remaining collagen scaffolds were manufactured without internal wire support. Scaffolds were sterilized with cold ethylene oxide gas prior to seeding with chondrocytes.

Example 2. Chondrocyte Isolation and Culture

Chondrocytes were isolated from auricular cartilage of 11-month-old sheep. Ear skin, subcutaneous tissues, and perichondrium were removed and discarded. Cartilage was minced into 1 $mm^3$ fragments and digested with 0.1% collagenase type II (Worthington Biochemical Corp., Lakewood, N.J.) at 37° C. for 16 hr. Isolated chondrocytes were washed twice with phosphate buffered saline (PBS); cells were counted using trypan blue and a hemocytometer and plated into roller bottles (Corning Inc., Acton, Mass.) at $3\times10^3$ cells/$cm^2$. Chondrocytes were cultured for approximately 10 days in culture medium, which consisted of Ham's F12 medium (Invitrogen, Grand Island, N.Y.) supplemented with 10% FBS (Sigma-Aldrich, St. Louis, Mo.), 100 U/mL penicillin, 100 µg/mL streptomycin, and 292 µg/mL L-glutamine (Sigma-Aldrich), 0.1 mM non-essential amino acids (Invitrogen), and 50 µg/mL ascorbic acid (Sigma-Aldrich). Upon reaching confluence, the chondrocytes were trypsinized with 0.05% trypsin-EDTA and used for this example.

Example 3. Cell Seeding and Construct Culture

Chondrocytes were suspended in culture medium at a concentration of $50\times10^6$ cells/mL. One mL of cell suspension was pipetted onto each scaffold and the cells were allowed to adhere for three hours with the scaffolds flipped upside down every 20 min to facilitate more uniform distribution of cells. Constructs were cultured in 6-well plates in 4 mL of culture medium on the platform of an orbital RotoMix mixer (Krackeler Scientific Inc., Albany, N.Y.), which was rotating at 55 rpm in standard incubator conditions (37° C. and 5% $CO_2$) for 2 days or 14 days. Vunjak-Novakovic et al., 42 J. Am. Inst. Chem. Engin. 850 (1996). The culture medium was changed twice a week.

Alternatively, each scaffold was placed into a 50 mL polypropylene tube with a 30×40 mm gas-permeable silicone window in 10 mL culture medium. Tubes were placed in a holder and rotated on a roller bottle apparatus at 1 rpm. The culture medium was changed twice a week. No difference was observed between the roller bottle and RotoMix incubation conditions.

Example 4. Construct Implantation

All procedures were approved by the Institutional Animal Care and Use Committee of the Massachusetts General Hospital and performed according to the National Institutes of Health Guidelines for the Care and Use of Laboratory Animals. Sixteen ear-shaped constructs, eight with wire support and eight without, were implanted subcutaneously on the backs of 6-8 week-old female athymic nude mice (Cox-7 Laboratories, Massachusetts General Hospital, Boston, Mass.), one construct per mouse. General anesthesia was achieved with intraperitoneal injection of 300 mg/kg-500 mg/kg tribromoethanol. Under aseptic conditions, a horizontal incision was performed 1.5 cm proximally from the base of the tail, and a subcutaneous pocket was created through blunt dissection. After insertion of the ear-shaped construct, the skin was closed with non-resorbable monofilament suture that was removed after 7 days. Additionally, in separate mice, four 5 mm diameter discs were implanted to serve as acellular controls; these discs were punched out of a 2 mm thick sheet of fibrous collagen identical to the ear-shaped scaffold material (Kensey Nash Corp.).

Alternatively, constructs were implanted in sheep to demonstrate autologous cartilage formation in a large, immunocompetent animal model. Four days before implantation, fetal bovine serum in culture medium was replaced with autologous sheep serum. Constructs were implanted subcutaneously in the neck; titanium rings, 12 mm in diameter, were placed around the implants to help locate the implant at explant. No immunosuppressive therapy was administered. At 6 weeks, the sheep were sacrificed. Half of the implants were dissected carefully and photographed; half were removed en bloc with surrounding tissue. All specimens were fixed in 10% formalin, embedded in paraffin, and sectioned at 5 µm. Sections were stained with hematoxylin and eosin (H&E), safranin-O, and toluidine blue. Immunohistochemical staining for collagen type I and II was performed.

Example 5. Gross Evaluation and Histology

The length and width of all constructs were measured with a sterilized digital caliper by three blinded observers at four time points: before seeding, after in vitro culture on days 2 or 14, and after 6 weeks in vivo.

The implants were harvested at 6 weeks and carefully dissected from the surrounding mouse tissue. For histological evaluation, full-thickness 5 mm diameter biopsies were punched at three areas of constructs with wire; complete cross sections were obtained at the similar levels from the constructs without wire. Three full-thickness, 5 mm-diameter biopsies for biochemical testing were obtained from similar locations in both types of constructs. Samples for histology were fixed in 10% buffered formalin. Specimens for biochemical testing were snap-frozen and stored at −80° C. until analyzed. To assess cartilage formation within wire coils, wires were carefully removed from the fixed tissue prior to paraffin embedding.

Paraffin-embedded specimens were sectioned at 5 Sections were stained with hematoxylin and eosin (H&E); cartilage ECM formation was evaluated with safranin O, toluidine blue, and Verhoeff's elastic stains.

For immunohistochemistry, tissue sections were pretreated with 1 mg/mL pepsin in Tris HCl (pH 2.0) for 15 min at room temperature, followed by peroxidase block and serum block from M.O.M. kit (Vector Laboratories Inc., Burlingame, Calif.). Sections were incubated with mouse anti-human collagen type I antibody (Accurate Chemical & Scientific Corp., Westbury, N.Y.) or mouse anti-human collagen type II antibody (Developmental Studies Hybridoma Bank, Iowa City, Iowa) for 30 min. EnVision+System Peroxidase kit (Dako, Carpinteria, Calif.) was used to identify the antigens; sections were counterstained with hematoxylin.

Example 6. Quantitative DNA and ECM Analyses

Frozen samples were weighed, minced and digested with 10% proteinase K from tritirachium album (Sigma-Aldrich Co.) at 56° C. overnight; the DNA was extracted and purified with a Qiagen DNeasy kit (Qiagen Inc., Valencia, Calif.) according to the manufacturer's instructions. Total DNA content was determined using a PicoGreen dsDNA assay. Singer et al., 249 Anal. Biochem. 228 (1997).

For biochemical analysis, engineered constructs and native sheep ear cartilage specimens were minced and lyophilized for 24 hr. The dehydrated specimens were weighed and digested with papain solution (125 µg/mL papain type III, 100 mM phosphate, 10 mM 1-cysteine, and 10 mM EDTA, pH 6.3) at 60° C. for 16 hours. Aliquots of these digests were assayed for glycosaminoglycan (GAG) and hydroxyproline (OH-proline) content. GAG content was measured spectrophotometrically using dimethylmethylene blue dye from the Blyscan Glycosaminoglycan Assay kit (Biocolor, Ltd. Carrickfergus, UK) with chondroitin sulfate as a standard. Enobakhare et al., 243 Anal. Biochem. 189 (1996). OH-proline content was measured in the aliquots of the same papain digests using Stegemann's hydroxyproline assay. Stegemann & Stalder, 18 Clin. Chim. Acta 267 (1967). All samples and standards were analyzed in duplicate.

Statistical Analysis:

Construct size and biochemical analyses values are expressed as mean±standard deviation. Statistical analyses were performed using SPSS 11.0 (SPSS, Chicago, Ill.). Comparison of means was assessed by a one-way analysis of variance (ANOVA) and the Tukey multiple comparison test ($p<0.05$ was considered significant).

Example 7. Engineering Flexible Cartilage in a Nude Rat

Figure 10:
FIG. 10 is a photograph of an embodiment of the present invention implanted on the back of a nude rat, 5 weeks after implantation.

Titanium frameworks were bent to mimic the shape of adult size human ear. Ear-shaped composite scaffolds were manufactured from coiled titanium wire frameworks and fibrous bovine dermis-derived type I collagen. Sheep auricular chondrocytes were expanded in vitro until sufficient numbers of cells were obtained, and 100 million chondrocytes were seeded onto the scaffold. The seeded construct was cultured in vitro for 3 weeks, and then implanted subcutaneously on the back of a nude rat. No complications were observed for the duration of the study. The ear remained well-formed and stable in vivo, until animal sacrifice at 5 weeks (FIG. 10). The flexibility and elastic deformation of the implant was tested by manipulation: the implanted ear was manually grasped, bent nearly in half so the top and bottom edges of the ear touched, and yet the ear-shaped construct returned to its original shape upon release. Histologically, neocartilage formation was noted in three biopsies obtained from wire-free areas of the explant (FIG. 11).

Example 8. Engineering a Replacement Autologous Outer Ear in a Sheep Model

Figure 12:
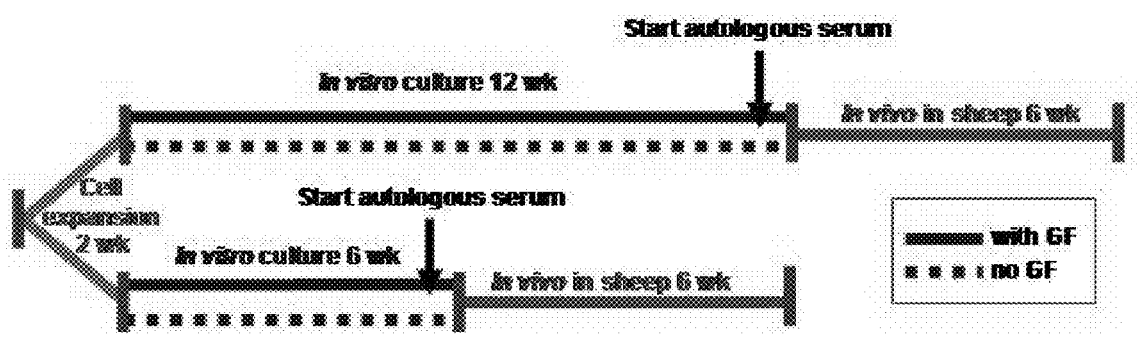
FIG. 12 is a scheme showing the experimental design of the current sheep study. In vitro culture periods were 6 weeks and 12 weeks; culture of seeded constructs was performed with and without supplementation with growth factors (GF).

To achieve a reproducible and robust neocartilage formation in an immunocompetent animal model, cartilage was matured in vitro prior to implantation. Mature neocartilage matrix protects bovine-derived collagen scaffold fibers and the antigen-presenting chondrocyte surface from active immunological responses of the immunocompetent subcutaneous environment during wound healing. Haisch et al., 2010. In this Example, in vitro culture time was increased to 6 wks. Growth factors were included in the culture medium to attempt to enhance the rate of neocartilage formation. Culture medium was supplemented with 100 ηg/mL insulin-like growth factor 1 (IGF-1) or 100 ηg/mL IGF+10 ηg/mL basic fibroblast growth factor (bFGF). Pei et al., 2002; Blunk et al., 2002). The experimental design is presented in FIG. 12.

Figure 13:
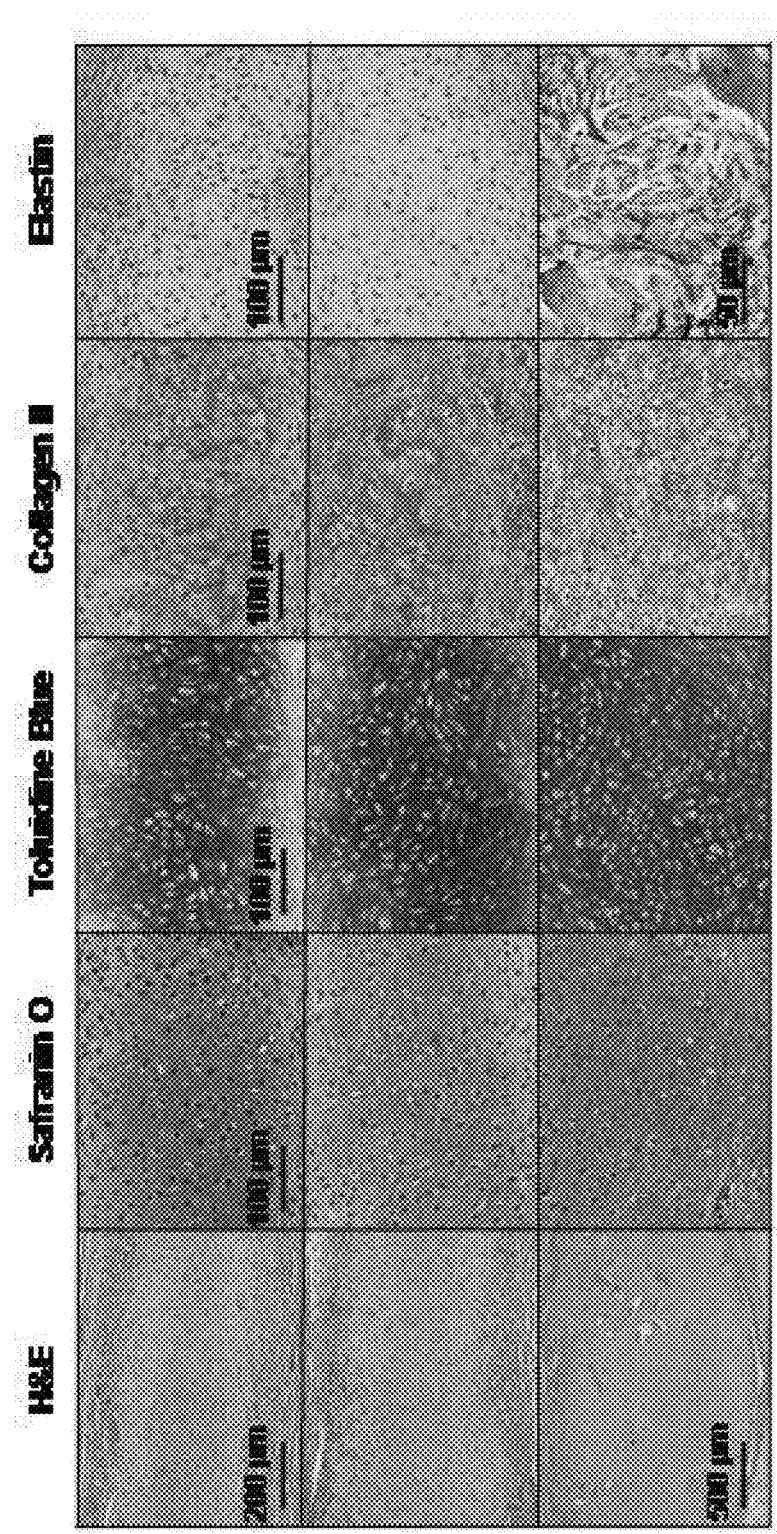
FIG. 13 shows histological images of the constructs explanted from sheep at 6 weeks, which constructs had been cultured in vitro for 6 weeks either with or without growth factor supplementation. Significantly thicker cartilage and elastin fiber formation are seen in the IGF/bFGF group. Only mild cellular inflammatory reaction and foreign body response were found in all groups at the periphery of the implants. Hematoxylin and eosin staining.

Fibrous collagen (Kensey Nash Corp.) scaffolds seeded with sheep auricular chondrocytes were incubated in culture medium with and without growth factor supplementation for 6 weeks (a similar approach incubates the chondrocyte-seeded scaffold for 12 weeks), and implanted subcutaneously on the neck of the sheep. After 6 weeks in vivo, contiguous neocartilage formation was present in all conditions with significantly thicker cartilage and elastin fiber formation in the IGF/bFGF group (FIG. 13) and normal cartilage morphology in all groups (FIG. 13 insets). Only mild cellular inflammatory reaction and foreign body response were found in all groups at the periphery of the implants. Cartilage made without adding growth factors to cell culture medium resembled that engineered as discussed elsewhere herein. More robust cartilage formation was achieved when growth factors were added to medium during in vitro culture.

Example 9. Scaffolds Comprising Mesenchymal Stem Cells

For scaffolds, fibrous collagen material was selected based on the prior screening studies in nude mice. Two mm thick sheets of material were manufactured by the Kensey Nash Corporation. Disks, 5 mm in diameter, were punched out of the sheets using dermal punches and sterilized by cold ethylene oxide gas.

Chondrocytes were isolated from sheep auricular cartilage. Skin, subcutaneous tissues, and perichondrium were removed in a single layer and discarded. Cartilage was minced into 1 mm$^3$ fragments and digested with 0.1% collagenase type II at 37° C. for 16 hr. Digested cartilage was washed repeatedly and cells counted. Chondrocytes were plated at $3\times10^3$ cells/cm$^2$ and cultured in roller bottles rotating at 1 rpm. Cells were cultured in standard chondrocyte medium (Ham's F12 medium, supplemented with 10% FBS, 0.1 mM non-essential amino acids, 100 U/mL penicillin, 100 μg/mL streptomycin, 292 μg/mL L-glutamine, and 50 μg/mL ascorbic acid) until subconfluent. Medium was changed twice weekly at which time it was collected, centrifuged to pellet debris, and used as culture medium for bone marrow derived mesenchymal stem cells (MSC).

Bone marrow was aspirated from the iliac crests of sheep under general anesthesia prior to ear cartilage harvest. Approximately 100 ml of marrow was collected into syringes containing 10 ml of 1000 U/ml heparin. Collected marrow was washed repeatedly with DMEM and plated into roller bottles in DMEM high glucose, supplemented with 10% FBS, 100 U/mL penicillin, and 100 μg/mL streptomycin. After 4 days, all non-adherent cells were removed and DMEM medium was replaced with chondrocyte-conditioned medium. The following experimental and control groups were created with and without transforming growth factor-β3 (TGF-β3):

Group 1: conditioned medium with 10 ηg/ml TGF-β3
Group 2: control medium with 10 ηg/ml TGF-β3
Group 3: conditioned medium without TGF-β3
Group 4: control medium without TGF-β3

MSCs were proliferated until sufficient number of cells was achieved at passage #2, at which time the cells were seeded onto 5 mm diameter/2 mm thick collagen scaffolds. Briefly, cell suspension ($50\times10^6$ cells/ml) was pipetted onto the scaffolds and cells were allowed to adhere for 3 hr with the scaffolds flipped upside down every 20 min.

Each scaffold was placed in a well of a 12-well plate in 1.5 ml of culture medium; the well plates were placed in standard incubator conditions and the constructs were cultured in vitro for 2 weeks.

The constructs were implanted subcutaneously on the dorsum of nude mice for 6 wk or 12 wk. After sacrifice, implants were carefully dissected, photographed, fixed in 10% formalin, embedded in paraffin, and sectioned at 5 μm. Cartilage matrix formation was evaluated with H&E, safranin-O, toluidine blue, and elastic stains. Immunohistochemical staining for collagen type II was performed. Gene expression for a marker of MSC chondrogenic differentiation (type II collagen, COL2A1) was assessed by polymerase chain reaction (PCR). Explanted constructs were evaluated for glycosaminoglycan (GAG) content, one of the most abundant components of cartilage matrix. GAG content was measured spectrophotometrically using dimethylmethylene blue dye from the BLYSCANT™ Glycosaminoglycan Assay kit (Biocolor, Ltd., Carrickfergus, UK) with chondroitin sulfate as a standard. Total DNA content was determined using a PICOGREEN® dsDNA assay (Invitrogen, Carlsbad, Calif.).

Due to their ability to differentiate into distinctive end-stage cell types, MSCs can be used for reforming many mesenchymal tissues, including cartilage, through the principles of tissue engineering. Caplan, 213 J. Cell. Physiol. 341 (2007). It has been demonstrated previously that incubation of MSCs with chondrocyte-conditioned medium in micromass culture significantly enhanced the production of cartilage specific matrix including type II collagen. Bauer, 124 Plast. Roconstr. Surg. 14e (2009).

Figure 14:
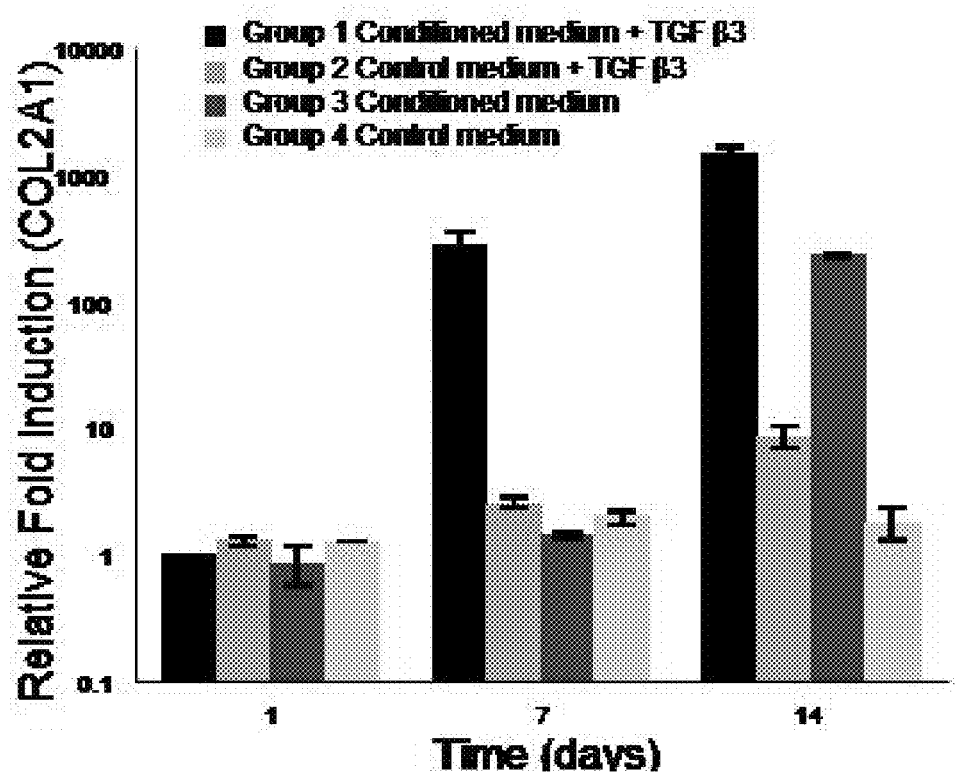
FIG. 14 reflects collagen type II gene expression during in vitro culture of constructs seeded with mesenchymal stem cells (MSC) proliferated and cultured in four conditions. COL2A1 was upregulated in group 1 after 7 days in vitro culture; it continued to be upregulated at 14 days. In group 3, collagen type II gene was upregulated by day 14.

Gene expression analysis was performed from constructs seeded with MSCs, proliferated, and cultured in four in vitro conditions prior to implantation into immunocompromised mice (FIG. 14): group 1: conditioned medium with 10 ηg/ml TGF-β3; group 2: control medium with 10 ηg/ml TGF-β3; group 3: conditioned medium without TGF-β3; and group 4: control medium without TGF-β3. COL2A1 was upregulated in group 1 after 7 days in vitro culture, and continued to be upregulated at 14 days. In group 3, the collagen type II gene was upregulated by day 14. In other groups, no changes occurred. Ten-fold induction occurred in control medium supplemented with TGF-β3. GAG content (FIG. 15) was elevated in group 1 after 7 days and was further elevated by day 14. In group 3, elevated GAG content was found on day 14. Supplementation of control medium with TGF-β3 lead to the increase of GAG content at day 14.

Figure 15:
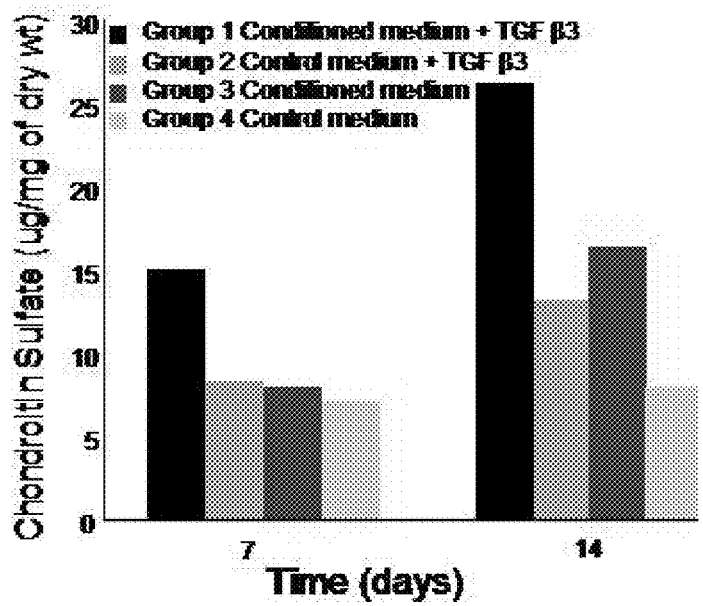
FIG. 15 is a bar graph showing GAG content during in vitro culture of constructs seeded with MSCs proliferated and cultured in four conditions. GAG content was elevated in group 1 after 7 days; it was further elevated by day 14. In group 3, elevated GAG content was found on day 14. Supplementation of control medium with TGF-β led to increased GAG content at day 14.
Figure 16:
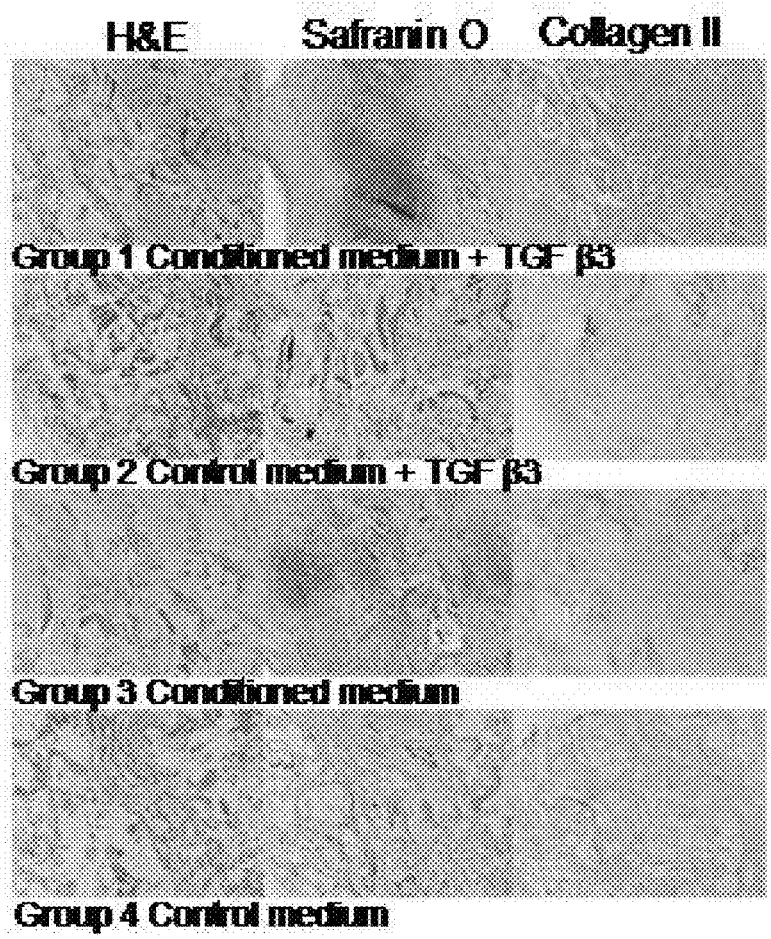
FIG. 16 presents histological images of cartilage engineered from MSCs proliferated and cultured in four conditions and implanted for 6 weeks in nude mice. Positive safranin-O and collagen type II staining in groups 1 and 3 indicated formation of engineered cartilage.
Figure 17:
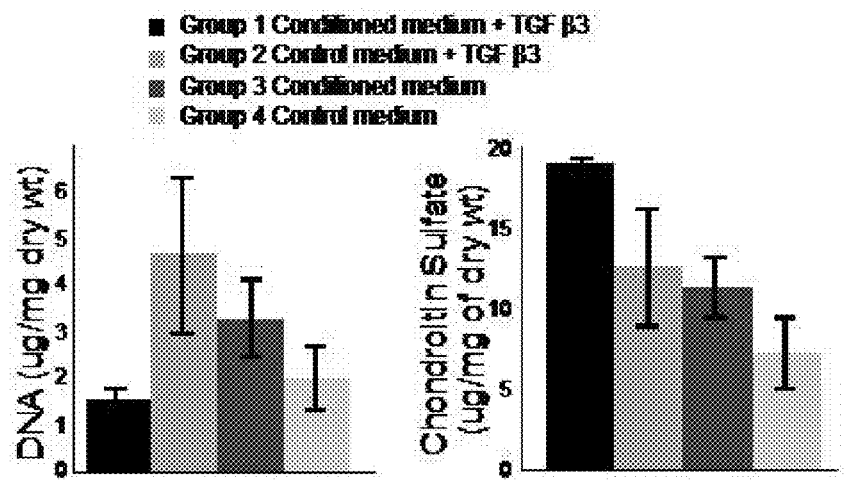
FIG. 17 is a bar graph reflecting DNA and GAG content of cartilage, engineered from MSCs and explanted from nude mice at 6 weeks. DNA content was the lowest in group 1. GAG content continued to be higher in group 1 as first observed during in vitro culture.

Implantation of MSC-seeded constructs into nude mice resulted in formation of cartilage-like tissue in groups 1 and 3 (FIG. 16). Positive safranin O and collagen type II staining in groups 1 and 3 indicated formation of engineered cartilage. Without chondrocyte conditioned medium, no cartilage could be detected in groups cultured in control medium, with and without TGF-β3 supplementation (groups 2 and 4 respectively). These in vitro culture conditions were maintained during MSC expansion and construct in vitro 2 week culture prior to implantation. DNA content (FIG. 17) was lowest in group 1, possibly attributed to more extensive MSC differentiation and, therefore, cessation of proliferation. GAG content (FIG. 17) continued to be higher in group 1 as first determined during in vitro culture. In general, GAG content remained unchanged compared to the data obtained prior to implantation (FIG. 15).

Figure 18:
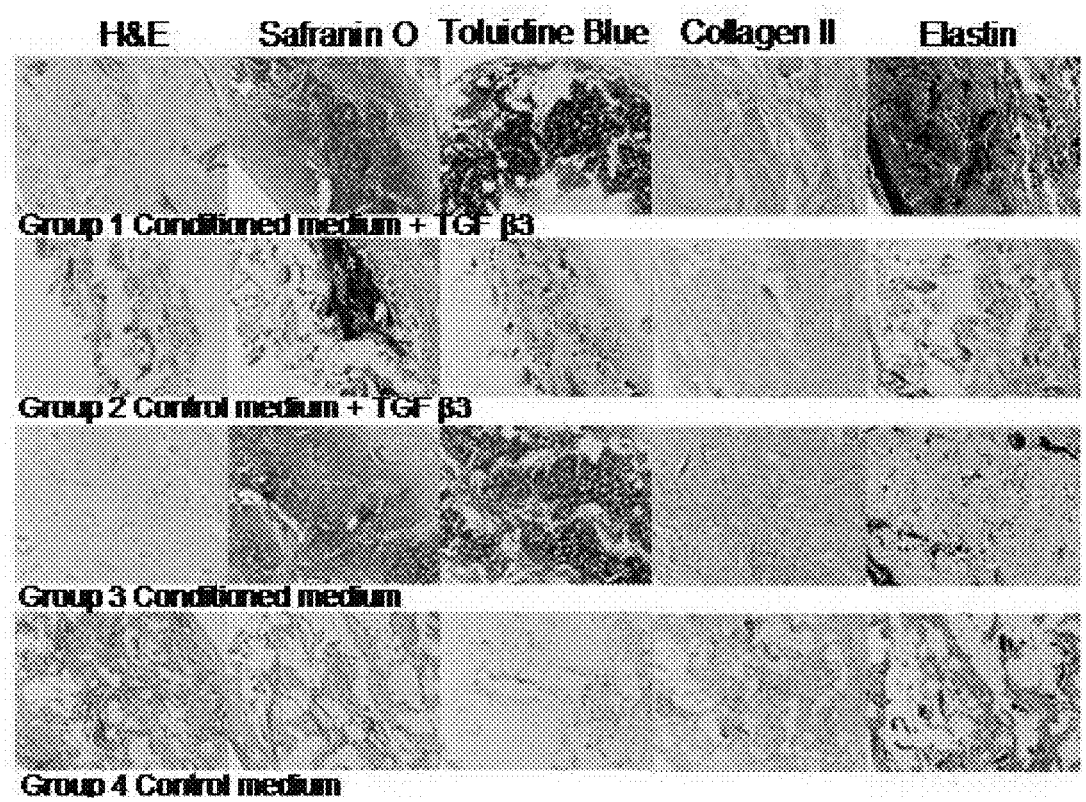
FIG. 18 shows histological images of cartilage engineered from MSCs proliferated and cultured in four conditions and implanted for 12 weeks in nude mice. Positive safranin-O, toluidine blue, and collagen type II staining in groups 1 and 3 indicated formation of engineered cartilage. Cartilage failed to form in groups 2 and 4.

Robust neocartilage formation was observed in MSC-seeded constructs from groups 1 and 3, 12 weeks after implantation in nude mice (FIG. 18). Positive safranin-O, toluidine blue, and collagen type II staining in groups 1 and 3 indicated formation of engineered cartilage. Cartilage failed, however, to form in groups 2 and 4 where MSCs were proliferated and cultured on the constructs in control, not chondrocyte conditioned, medium; regardless of supplementation with TGF-β3. Elastin fiber formation was seen in both groups 1 and 3, suggesting that soluble factors were secreted by chondrocytes into conditioned medium, which up-regulated the elastin gene expression in MSCs.

In conclusion, neocartilage formation was demonstrated in nude mice in constructs seeded with bone marrow derived sheep MSCs; these MSCs had been expanded and cultured in sheep chondrocyte-conditioned medium. Supplementation of conditioned medium with TGF-β3 resulted in more rapid cartilage matrix formation, and possibly more complete differentiation of MSCs. These studies address the issue of obtaining a cell source for engineering an adult sized human ear in the event autologous primary chondrocytes are unavailable due to extensive craniofacial injuries.

The invention claimed is:

1. A composition for craniofacial reconstruction comprising: a biocompatible scaffold; and a permanent bendable wire embedded within said scaffold; wherein the permanent bendable wire is configured into a framework that has torsional flexibility and a shape memory to allow the composition to be temporarily and substantially deformed on application of a force, and return to the pre-deformed shape upon removal of said force, and wherein the wire has a diameter of between 0.025 mm and 1.25 mm.

2. The composition of claim 1, wherein the framework comprises a wire framework comprising a central wire and a wire coil surrounding it; wherein the central wire has the shape of the prominent craniofacial feature and the surrounding coil provides surface area and loops for tissue integration.

3. The composition of claim 1, further comprising viable cells.

4. The composition of claim 3, wherein the viable cells are chondrocytes or mesenchymal stem cells.

5. The composition of claim 1, wherein the scaffold comprises at least one of collagen, chondrocyte/collagen, cartilage, silk, carbon fibers, silicone, polyethylene, polyglycolic acid, poly-L-lactic acid, or polycaprolactone.

6. The composition of claim 5, wherein the collagen is fibrous type I collagen, type II collagen, or recombinant collagen.

7. The composition of claim 1, wherein the framework comprises at least one metal or metal alloy, selected from the group consisting of gold, titanium, titanium alloy, nickel alloy, stainless steel, cobalt-chromium, and tantalum.

8. The composition of claim 7, wherein the framework comprises titanium wire.

9. The composition of claim 1, wherein the framework comprises tantalum over carbon.

10. The composition of claim 1, wherein the composition comprises cartilage.

11. The composition of claim 1, wherein the wire of the framework has a diameter of between 0.025 and 0.38 mm.

12. A composition for auricular reconstruction comprising: a biocompatible porous scaffold comprising fibrous collagen and having an auricular shape; a permanent titanium wire embedded within said scaffold; and viable cells distributed in said scaffold; wherein the permanent titanium wire is configured into an auricular shape and has resiliency, flexibility and strength for a shape memory that allows the composition to be temporarily and substantially-deformed upon application of a force and to return to the pre-deformed shape upon removal of said force, and wherein the titanium wire has a diameter of between 0.025 mm and 1.25 mm.

13. The composition of claim 12, wherein the titanium wire has a diameter of between 0.025 and 0.38 mm.

14. The composition of claim 12, wherein the titanium wire framework comprises a central wire and a wire coil surrounding it, wherein the central wire has the shape of the prominent ear features and the surrounding coil provides surface area and loops for tissue integration.

15. The composition of claim 12, wherein the cells are chondrocytes or mesenchymal stem cells.

16. The composition of claim 12, further comprising cartilage.

* * * * *